US012593997B1

(12) United States Patent
    Sanchez Terrones

(10) Patent No.: US 12,593,997 B1
(45) Date of Patent: Apr. 7, 2026

(54) BIOMETRIC RING AND ASSOCIATED METHODS

(71) Applicant: Promptus LLC, Greenwood Village, CO (US)

(72) Inventor: Benjamin Sanchez Terrones, Chicago, IL (US)

(73) Assignee: Promptus LLC, Greenwood Village, CO (US)

( * ) Notice: Subject to any disclaimer, the term of this patent is extended or adjusted under 35 U.S.C. 154(b) by 0 days.

(21) Appl. No.: 19/312,303

(22) Filed: Aug. 28, 2025

Related U.S. Application Data

(60) Provisional application No. 63/825,445, filed on Jun. 17, 2025.

(51) Int. Cl.
    *A61B 5/024* (2006.01)
    *A61B 5/00* (2006.01)
    *A61B 5/256* (2021.01)
    *A61B 5/307* (2021.01)

(52) U.S. Cl.
    CPC ...... *A61B 5/02438* (2013.01); *A61B 5/02444* (2013.01); *A61B 5/256* (2021.01); *A61B 5/307* (2021.01); *A61B 5/6826* (2013.01); *A61B 5/7271* (2013.01); *A61B 2562/043* (2013.01)

(58) Field of Classification Search
    CPC ...... A61B 5/681; A61B 5/6826; A61B 5/6824
    See application file for complete search history.

(56) References Cited

U.S. PATENT DOCUMENTS

| | | | |
|---|---|---|---|
| 9,711,060 B1 | 7/2017 | Lusted et al. | |
| 10,517,536 B1 | 12/2019 | Lusted | |
| 10,709,339 B1 | 7/2020 | Lusted | |
| 10,874,307 B2 | 12/2020 | Narasimhan et al. | |
| 11,868,178 B2 | 1/2024 | von Badinski et al. | |
| 12,228,968 B2 | 2/2025 | von Badinski et al. | |
| 2010/0168531 A1 | 7/2010 | Shaltis et al. | |
| 2019/0204865 A1 | 7/2019 | Von Badinski et al. | |
| 2023/0008487 A1 | 1/2023 | Caizzone et al. | |
| 2023/0085555 A1* | 3/2023 | Nomvar ............... | A61B 5/6843 |
| | | | 600/347 |
| 2024/0201736 A1 | 6/2024 | von Badinski et al. | |
| 2025/0181113 A1 | 6/2025 | von Badinski et al. | |

FOREIGN PATENT DOCUMENTS

| | | | | |
|---|---|---|---|---|
| WO | WO2010/0126827 | * 11/2010 | ............ | A61B 5/053 |
| WO | 2018005298 A1 | 1/2018 | | |
| WO | 2021032297 A1 | 2/2021 | | |
| WO | 2023281370 A1 | 1/2023 | | |
| WO | 2024006861 A2 | 1/2024 | | |
| WO | 2024013714 A1 | 1/2024 | | |

* cited by examiner

*Primary Examiner* — George R Evanisko
(74) *Attorney, Agent, or Firm* — Stephen B. Katsaros; Patent Engineering, LLC

(57) ABSTRACT

The present disclosure provides a biometric ring comprising an inner surface configured to adjoin a living being and a plurality of conductors circumferentially arranged about the inner surface. The conductors are configured to emit current and measure voltage across conductor path pairs. The biometric ring determines corresponding conductor path resistances through the body and generates resistance maps from these measurements. A biometric reading is derived from the resistance maps, enabling non-invasive monitoring of physiological parameters.

16 Claims, 12 Drawing Sheets

BIOMETRIC RING AND ASSOCIATED METHODS

CROSS REFERENCE TO RELATED APPLICATION

This application claims priority to U.S. Provisional Application No. 63/825,445 entitled "BIOMETRIC RING" filed Jun. 17, 2025, by Inventor Benjamin Sanchez, which is hereby incorporated by reference in its entirety.

TECHNICAL FIELD

The present invention relates to wearable biometric monitoring devices, particularly smart rings that utilize electrical impedance measurements to assess physiological parameters. Conventional wearable health monitors typically rely on optical sensors or single-point electrical measurements, which can be limited by factors such as skin pigmentation, device positioning, and measurement accuracy for parameters like blood pressure, blood flow, heart characteristics, etc.

BACKGROUND

Wearable electronic devices for health monitoring have gained widespread adoption, with smart rings representing a compact form factor that can be worn continuously on a user's finger. These devices typically incorporate sensors to measure various physiological parameters such as heart rate, temperature, and activity levels. Traditional wearable health monitors often rely on optical sensors or single-point electrical measurements to estimate health metrics. Still, these approaches can be limited by factors such as skin pigmentation, device positioning, and measurement accuracy for certain parameters like blood pressure.

U.S. Pat. No. 10,709,339 of Hugh Lusted discloses electrical conductors (EKG) for electrocardiography well-established diagnostic technique for monitoring heart electrical activity. This patent describes a ring with sensor surfaces on its inner surface comprising ECG and EDA electrodes positioned around a PPG (photoplethysmograph) module. The referenced EKG system functions as a low-voltage differential amplifier that detects potential differences on the skin resulting from ionic currents within the heart muscle during depolarization and repolarization phases. These cardiac activities generate small electrical charges-typically millivolts-that propagate through bodily tissues and create detectable voltage changes at the skin's surface (as noted in the references as " . . . provided to measure an EDA signal generated from electrodes that register changes in skin resistance."). The EKG measures these surface potential differences rather than mapping internal (i.e., cross-sectional) resistance or impedance. While other traditional EKG systems often use twelve leads, wearable health technology has enabled minimal electrode configurations, often just two surface-interfacing conductors. These wearable devices maintain the fundamental operating principle: measuring electrical potential differences between two spatially separated points on the skin. Unlike the present disclosure, EKG systems are not capable of measuring internal impedance or resistance, but rather of detecting time-varying voltage changes correlated to the skin.

SUMMARY

Continuous monitoring of blood pressure and cardiovascular health represents a critical need in modern healthcare, with over 1.28 billion adults worldwide suffering from hypertension according to the World Health Organization. Current blood pressure monitoring methods rely primarily on inflatable cuffs that provide only intermittent measurements, missing critical fluctuations that occur throughout the day. Existing wearable devices, such as smart rings and watches, typically use photoplethysmography (PPG) technology, which has significant limitations, including poor accuracy across different skin pigmentations and the inability to measure blood pressure directly. The present invention addresses these limitations by providing a novel approach to continuous, non-invasive blood pressure monitoring through electrical impedance measurements in a compact, wearable form factor.

According to an aspect of the present disclosure, a biometric ring is provided. The biometric ring comprises an inner surface configured to adjoin a living being. The biometric ring includes a plurality of conductors circumferentially arranged about the inner surface and configured to emit current and measure voltage (or vice versa). The biometric ring comprises a plurality of conductor path pairs comprising at least a primary conductor path pair, a secondary conductor path pair, and a tertiary conductor path pair. The biometric ring includes a plurality of conductor path resistances comprising at least a primary conductor path resistance, a secondary conductor path resistance, and a tertiary conductor path resistance. The biometric ring comprises a plurality of resistance maps derived from the plurality of conductor path resistances. The biometric ring includes a biometric reading derived from a plurality of resistance maps.

According to other aspects of the present disclosure, the biometric ring may include one or more of the following features. The inner surface may be configured to interface with a digit, an extremity, or a vascular-connected pathway of the living being. Each of the plurality of conductors may comprise a first conductor, a second conductor separated from the first conductor, and a resistance measured between the first conductor and the second conductor, the resistance operationally associated with a voltage potential and a current flow between the first conductor and the second conductor. The plurality of conductors may comprise at least four conductors. The biometric ring may further comprise a processor configured to perform a detection sequence that moves sequentially around the plurality of conductors. The detection sequence may be performed at a rate of 20-100 rotations per second. The biometric ring may further comprise a processor configured to apply voltage or current with a frequency between 20 kHz and 100 kHz. The biometric ring may further comprise a machine learning algorithm configured to correlate the plurality of resistance maps to a blood biometric reading. The machine learning algorithm may be configured to process successive frames of resistance map data collected over time. The biometric ring may further comprise analog front-end circuitry configured to direct the detection sequence using the plurality of conductors. The biometric ring may further comprise a wireless communication transceiver configured to transmit biometric reading data to an external device. The biometric ring may further comprise a processor configured to generate cross-sectional images based on the plurality of resistance maps. The cross-sectional images may be generated using at least one of the statistical reconstruction methods and deterministic reconstruction methods. The biometric ring may further comprise a processor configured to determine heart rate based on temporal changes in the plurality of resistance maps.

According to another aspect of the present disclosure, a method for biometric monitoring is provided. The method comprises positioning an inner surface to adjoin a living being. The method includes circumferentially arranging a plurality of conductors about the inner surface. The method comprises configuring the plurality of conductors to emit current and measure voltage. The method includes establishing a plurality of conductor path pairs comprising at least a primary conductor path pair, a secondary conductor path pair, and a tertiary conductor path pair. The method comprises determining a plurality of conductor path resistances comprising at least a primary conductor path resistance, a secondary conductor path resistance, and a tertiary conductor path resistance. The method includes generating a plurality of resistance maps derived from the plurality of conductor path resistances. The method comprises deriving a biometric reading from the plurality of resistance maps.

According to other aspects of the present disclosure, the method may include one or more of the following features. Positioning the inner surface may comprise interfacing with a digit, an extremity, or a vascular-connected pathway of the living being. Establishing the plurality of conductor path pairs may comprise providing a first conductor, providing a second conductor separated from the first conductor, and measuring a resistance between the first conductor and the second conductor, the resistance operationally associated with a voltage potential and a current flow between the first conductor and the second conductor. Circumferentially arranging the plurality of conductors may comprise providing at least four conductors. The method may further comprise performing a detection sequence that moves sequentially around the plurality of conductors. Performing the detection sequence may comprise operating at a rate of 20-100 rotations per second. The method may further comprise applying voltage or current with a frequency between 20 kHz and 100 KHz.

According to another aspect of the present disclosure, a biometric ring is provided. The biometric ring comprises an inner surface configured to adjoin a living being. The biometric ring includes a plurality of conductors circumferentially arranged about the inner surface and configured to emit voltage and measure voltage. The biometric ring comprises a plurality of conductor path pairs comprising at least a primary conductor path pair, a secondary conductor path pair, and a tertiary conductor path pair. The biometric ring includes a plurality of conductor path resistances comprising at least a primary conductor path resistance, a secondary conductor path resistance, and a tertiary conductor path resistance. The biometric ring comprises a plurality of resistance maps derived from the plurality of conductor path resistances. The biometric ring includes a biometric reading derived from a plurality of resistance maps.

According to other aspects of the present disclosure, the biometric ring may include one or more of the following features. The inner surface may be configured to interface with a digit, an extremity, or a vascular-connected pathway of the living being. The plurality of conductors may comprise a first conductor, a second conductor separated from the first conductor, and a resistance measured between the first conductor and the second conductor, the resistance operationally associated with a voltage potential and a current flow between the first conductor and the second conductor. The plurality of conductor path pairs may further comprise at least one of a quaternary conductor path pair, a quinary conductor path pair, a senary conductor path pair, and a septenary conductor path pair. The primary conductor path pair may comprise adjacent conductors within the plurality of conductors. The secondary conductor path pair may comprise conductors separated by one conductor within the plurality of conductors. The tertiary conductor path pair may comprise conductors separated by two conductors within the plurality of conductors. The biometric reading may comprise at least one of blood pressure, blood velocity, heart rate, and heart rate variability. The biometric ring may further comprise a processor configured to generate the plurality of resistance maps by correlating voltage measurements and current flows across the plurality of conductor path pairs.

According to another aspect of the present disclosure, a biometric monitoring system is provided. The biometric monitoring system comprises a ring-shaped device having an inner circumference with a plurality of conductive elements distributed around the inner circumference. The biometric monitoring system includes circuitry configured to apply electrical signals between different combinations of the conductive elements and measure resulting electrical responses through biological tissue. The biometric monitoring system comprises a processing unit configured to create electrical impedance tomography data from the measured electrical responses, process the electrical impedance tomography data to generate cross-sectional images of blood flow within the biological tissue, and extract physiological parameters from variations in the cross-sectional images over time.

According to another aspect of the present disclosure, a method for non-invasive blood biometric reading is provided. The method comprises positioning a plurality of electrical sensors in contact with skin around the circumference of a body appendage. The method includes applying a current between sequential pairs of the electrical sensors. The method comprises measuring voltage responses across the sequential pairs to determine electrical impedance values through the tissue of the body appendage. The method includes constructing a two-dimensional impedance map of the body appendage from the electrical impedance values. The method comprises analyzing temporal variations in the two-dimensional impedance map to identify blood flow patterns. The method includes correlating the blood flow patterns to blood biometric readings using a trained machine learning model.

Further areas of applicability of the present disclosure will become apparent from the detailed description provided hereinafter. It should be understood that the detailed description and specific examples, while indicating various configurations, are intended for purposes of illustration only and are not intended to limit the scope of the disclosure necessarily.

BRIEF DESCRIPTION OF THE DRAWINGS

The accompanying figures of the drawing, which are included to provide a further understanding of general aspects of the system/method, are incorporated in and constitute a part of this specification. These illustrative aspects of the system/method, together with the detailed description, explain the principles of the system. No attempt is made to show structural details in more detail than is necessary for a fundamental understanding of the system and the various ways in which it is practiced. The following figures of the drawing include.

Figure 1:
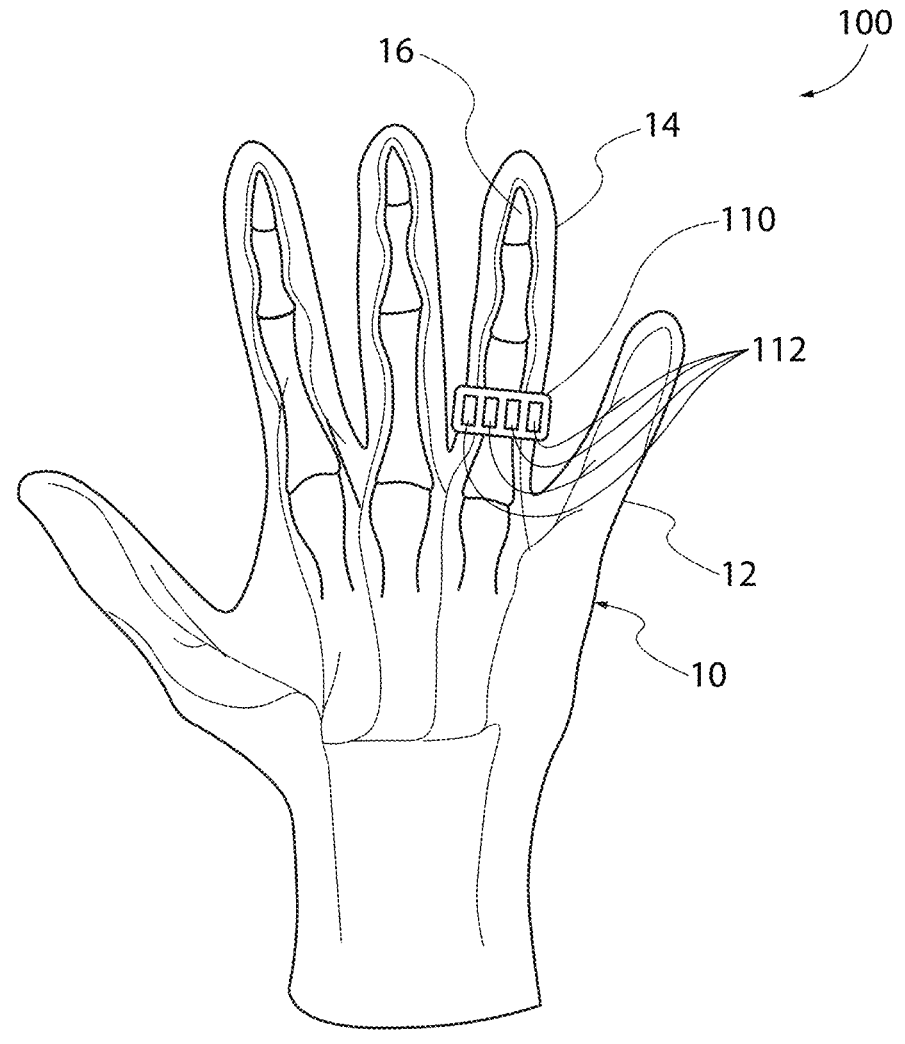
FIG. 1 illustrates a skeletal schematic with a biometric ring positioned on a human digit, consistent with embodiments of the disclosure.

In the appended figures, similar components and/or features may have the same reference label. Further, various components of the same type may be distinguished by following the reference label with a dash and a second label that distinguishes among the similar components. If only the first reference label is used in the specification, the description applies to any one of the similar components having the same first reference label, irrespective of the second reference label. Where the reference label is used in the specification, the description applies to any one of the similar components having the same reference label.

DETAILED DESCRIPTION

Illustrative configurations are described with reference to the accompanying drawings. Wherever convenient, the same reference numbers are used throughout the drawings to refer to the same or similar parts. While examples and features of disclosed principles are described herein, modifications, adaptations, and other implementations are possible without departing from the spirit and scope of the disclosed configurations. It is intended that the following detailed description be considered exemplary only, with the true scope and spirit being indicated by the following claims.

Conventional wearable health monitoring devices face substantial limitations in accurately measuring cardiovascular parameters such as blood pressure and blood flow. Traditional photoplethysmogram (PPG) technology, commonly used in smart rings and fitness trackers, relies on optical sensors that detect changes in light transmission through tissue to estimate blood volume variations. However, PPG technology demonstrates inconsistent performance across different skin pigmentations and fails to provide a direct correlation to actual blood pressure measurements. The optical approach may be affected by ambient light conditions, motion artifacts, and variations in skin thickness, leading to unreliable readings. Additionally, conventional devices typically require placement at specific high blood flow areas, such as the wrist, to achieve acceptable accuracy levels. Single-point electrical measurement systems also present challenges, as these systems can only capture limited information about the complex three-dimensional structure of blood vessels and tissue conductivity within a given anatomical region.

The disclosed biometric ring technology addresses these limitations through a novel approach that employs multiple conductors circumferentially arranged around an inner surface of a ring-shaped housing. This configuration enables comprehensive electrical impedance measurements across the entire cross-sectional area of a finger or other body appendage. The system applies controlled electrical currents between different pairs of conductors and measures the resulting voltage responses to create detailed resistance maps of the underlying tissue. By utilizing multiple conductor path pairs, including primary, secondary, and tertiary conductor path configurations, the system can generate cross-sectional images that reveal blood flow patterns and vascular characteristics with enhanced precision. The electrical impedance approach provides direct measurement of tissue conductivity changes associated with blood volume variations, offering improved accuracy compared to optical methods. Furthermore, the circumferential arrangement of conductors allows the device to function effectively regardless of rotational positioning on the finger, eliminating the need for precise placement that constrains conventional monitoring systems. Machine learning algorithms process the temporal variations in resistance maps to extract physiological parameters such as blood pressure, blood velocity, heart rate, and heart rate variability, providing comprehensive cardiovascular monitoring capabilities in a compact, wearable form factor.

FIG. 1 illustrates a skeletal schematic with a biometric ring 100 showing the overall system placement on a human hand according to various configurations. The skeletal schematic with a biometric ring 100 may include an extremity 10, a hand 12, a digit 14, a bone 16, a biometric ring 110, and a plurality of conductors 112. The skeletal schematic with a biometric ring 100 demonstrates how the biometric ring 110 interfaces with anatomical structures to enable non-invasive biometric monitoring through electrical impedance measurements across tissue layers.

The extremity 10 represents the anatomical structure that supports the biometric monitoring system and provides the biological interface for electrical measurements. The extremity 10 may include various body parts that can be circumscribed and have sufficient blood flow to render accurate biometric measurements. In some cases, the extremity 10 may be a wrist, neck, ankle, or any body part that allows for circumferential placement of the monitoring device. The extremity 10 contains vascular networks and tissue structures that exhibit varying electrical impedance properties based on blood flow dynamics and physiological changes over time.

The hand 12 forms part of the extremity 10 and provides a specific anatomical location for biometric ring placement. The hand 12 may include skeletal structures, muscles, tendons, nerves, digital arteries, and blood vessels surrounded by fatty tissue and skin layers. The hand 12 offers multiple potential placement sites for the biometric ring 110, with each digit providing access to vascular pathways suitable for electrical impedance monitoring. Additionally, the hand 12 contains varying tissue densities and blood vessel configurations that create distinct electrical impedance signatures detectable by the plurality of conductors 112.

In an illustrative configuration, the digit 14 serves as the primary interface location for the biometric ring 110 and represents the specific anatomical structure where electrical measurements occur. The digit 14 may include internal structures such as bones, blood vessels, capillaries, fatty tissue, and skin layers that exhibit different electrical conductivity properties. The digit 14 provides a circumferential surface area that allows the biometric ring 110 to maintain consistent contact with skin tissue while enabling electrical current pathways through various tissue types. Moreover, the digit 14 contains sufficient vascular density to generate detectable impedance variations corresponding to blood flow changes and cardiovascular dynamics.

The bone 16 represents the skeletal structure within the digit 14 that influences electrical impedance measurements and provides anatomical reference points for cross-sectional imaging. The bone 16 may exhibit distinct electrical properties compared to surrounding soft tissues, creating impedance contrasts that enhance the resolution of electrical measurements. The bone 16 serves as a relatively stable anatomical landmark that helps define the internal geometry of the digit 14 during electrical impedance tomography processes. Consequently, the bone 16 contributes to the overall impedance map generated by the plurality of conductors 112 and provides a structural context for interpreting biometric data.

The biometric ring 110 comprises the primary monitoring device that houses the electrical measurement system and interfaces directly with the digit 14. The biometric ring 110 may include an inner surface configured to adjoin a living being and maintain consistent electrical contact with skin tissue. The biometric ring 110 can be worn on body parts other than fingers, such as wrists, necks, ankles, or any body part that can be circumscribed and has sufficient blood flow for biometric measurements. Alternatively, the biometric ring 110 may be replaced with a band that has a closed band-shaped loop form factor, but may not necessarily be round to accommodate body parts that may not conform to a circular configuration. Furthermore, the biometric ring 110 or alternative band may be flexible and elastic to conform closely with the contours of the user's body that the biometric ring 110 or alternative band circumscribes.

In an illustrative configuration, the plurality of conductors 112 comprises the electrical sensing elements that enable impedance measurements across tissue structures within the digit 14. The plurality of conductors 112 may be circumferentially arranged about the inner surface of the biometric ring 110 and configured to emit current and measure voltage (wherein some individual conductors emit current while others measure voltage in an cyclical manner) across various tissue pathways. The plurality of conductors 112 can generate electrical fields that penetrate through skin, fatty tissue, blood vessels, and other anatomical structures to create comprehensive impedance maps of the digit 14 cross-section. Additionally, the plurality of conductors 112 may be configured to emit voltage and measure voltage responses to determine electrical impedance values through different conductor path combinations. The plurality of conductors 112 enables the biometric ring 110 to interface with a digit, an extremity, or a vascular-connected pathway of the living being through systematic electrical measurements that correlate with physiological parameters such as blood flow, blood pressure, and cardiovascular dynamics.

Figure 2:
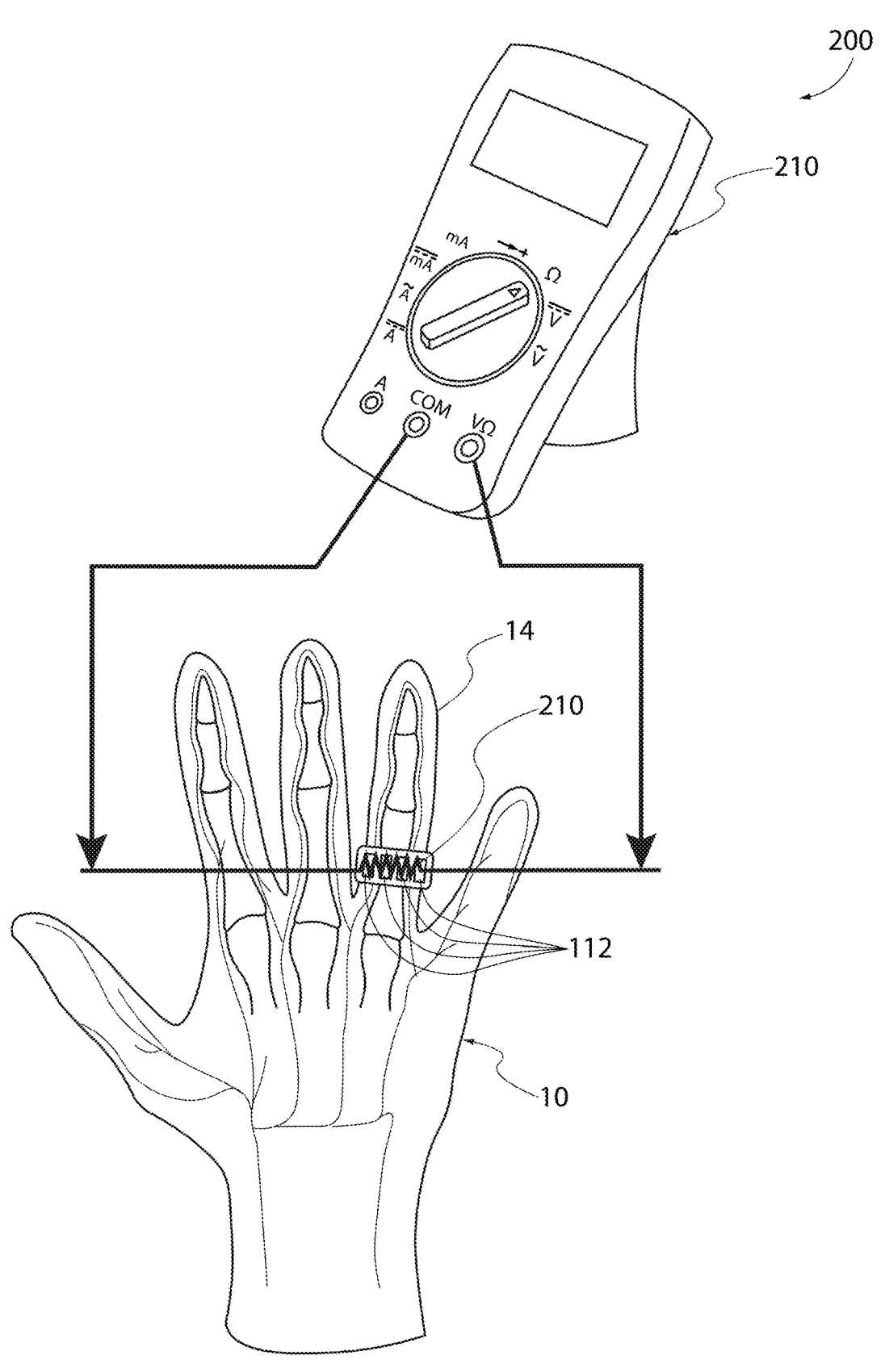
FIG. 2 illustrates a resistance measurement schematic showing electrical measurement through human tissue using a meter, consistent with embodiments of the disclosure.

FIG. 2 illustrates a resistance schematic 200 demonstrating the electrical measurement principles utilized by the biometric ring 110 for obtaining biometric readings through the digit 14. The resistance schematic 200 may include a meter 210 connected to the plurality of conductors 112 positioned around the digit 14, enabling precise measurement of electrical properties through biological tissue. The configuration shown in the resistance schematic 200 demonstrates how voltage and current measurements can be obtained between different conductor pairs to calculate resistance values that correlate to physiological parameters within the digit 14.

The meter 210 disclosed in the resistance schematic 200 may include digital measurement capabilities for accurately determining electrical resistance values through the biological tissue of the digit 14. The meter 210 can be configured to apply controlled voltage or current signals between selected pairs of the plurality of conductors 112 and measure the resulting electrical responses. In some cases, the meter 210 may operate at frequencies between 20 kHz and 100 kHz to optimize signal penetration through the tissue while maintaining measurement accuracy. The meter 210 additionally may include analog-to-digital conversion circuitry to process the measured signals and convert them into digital data suitable for further analysis by processing components within the biometric ring 110.

The resistance 210 measurements obtained through the configuration shown in the resistance schematic 200 may be calculated based on the fundamental relationship between voltage potential and current flow through the biological tissue. When a first conductor from the plurality of conductors 112 applies a known current or voltage to the digit 14, and a second conductor separated from the first conductor measures the resulting electrical response, the resistance 210 can be determined using Ohm's law principles. The resistance 210 values may vary based on the blood flow, tissue composition, and physiological state within the digit 14, providing the basis for biometric measurements. Moreover, the resistance 210 measurements can be collected sequentially between different conductor path pairs to create a comprehensive electrical impedance map of the cross-sectional area of the digit 14.

In an illustrative configuration, the plurality of conductors 112 shown in the resistance schematic 200 may be constructed from biocompatible and non-corroding materials to ensure safe contact with the skin of the digit 14. The plurality of conductors 112 can be fabricated from precious metals, including gold, silver, and alloys thereof, which provide excellent electrical conductivity while maintaining biocompatibility for extended skin contact. Alternatively, the plurality of conductors 112 may be constructed from stainless steel or platinum iridium, which offer durability and corrosion resistance in biological environments. The number of conductors within the plurality of conductors 112 may range from as few as four to as many as sixteen, with eight total conductors illustrated as an example configuration that provides adequate spatial resolution for cross-sectional imaging of the digit 14.

The electrical connection between the plurality of conductors 112 and the skin surface of the digit 14 may be enhanced through the use of conductive media to improve signal quality and measurement accuracy. A conductive medium, such as Poly(3,4-ethylenedioxythiophene) or PEDOT, can be applied to facilitate the electrically conductive connection between the epidermis and the plurality of conductors 112. The conductive medium may reduce contact impedance and provide more stable electrical coupling between the conductors and the skin surface. In some cases, natural secretions from the epidermis, such as sweat and oils, may provide adequate conductivity for the resistance 210 measurements without requiring additional conductive media, particularly when the biometric ring 110 maintains proper contact pressure against the digit 14.

The resistance schematic 200 demonstrates how sequential measurements between different conductor pairs enable the creation of a comprehensive electrical impedance profile of the digit 14. The first conductor and second conductor separated from the first conductor can be selected from the plurality of conductors 112 in various pairing configurations to obtain resistance measurements across different paths through the biological tissue. The resistance operationally associated with a voltage potential and a current flow between the first conductor and the second conductor provides data points that can be processed to generate cross-sectional images of blood flow patterns within the digit 14. Consequently, the resistance schematic 200 illustrates the fundamental measurement principle that enables the biometric ring 110 to non-invasively monitor cardiovascular parameters through electrical impedance tomography techniques applied to the digit 14.

Figure 3:
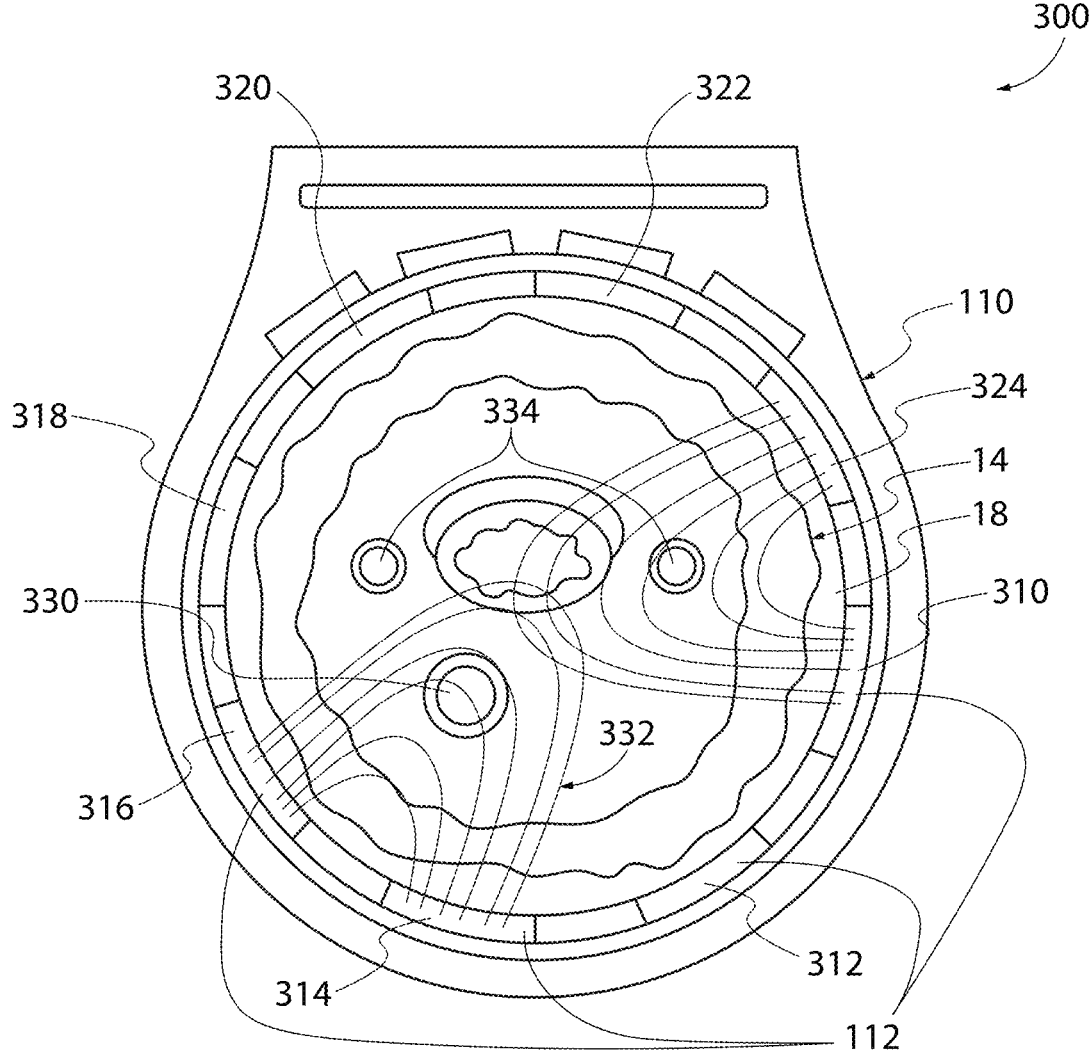
FIG. 3 illustrates a cross-sectional view of a finger and biometric ring showing multiple conductors and electrical fields, consistent with embodiments of the disclosure.

FIG. 3 illustrates an illustrative cross-sectional view of a finger and a biometric ring 300 showing the detailed arrangement of conductors and electrical field patterns within biological tissue. The illustrative cross-sectional view of finger and biometric ring 300 may include a first conductor 310, a second conductor 312, a third conductor 314, a fourth conductor 316, a fifth conductor 318, a sixth conductor 320, a seventh conductor 322, an eighth conductor 324, a blood vessel 330, an electrical field 332, capillaries 334, and skin 18. The cross-sectional perspective reveals how the biometric ring 110 interfaces with the digit 14 to enable electrical impedance measurements through biological tissue layers.

The first conductor 310 may be positioned at a specific angular location around the inner circumference of the biometric ring 110, serving as one terminal for electrical current application. The first conductor 310 can be fabricated from biocompatible materials such as gold, silver, platinum, iridium, or stainless steel to ensure safe contact with the skin 18. When activated, the first conductor 310 may emit current that travels through the digit 14 tissue to reach other conductors in the array. The electrical properties of the first conductor 310 allow for precise voltage measurements that contribute to resistance mapping across the cross-sectional area of the digit 14. Additionally, the first conductor 310 may be configured to operate at frequencies between 20 kHz and 100 kHz, with 50 kHz representing one operational frequency that accommodates different user sensitivities.

The second conductor 312 may be positioned adjacent to the first conductor 310 or separated by one or more intermediate conductors, depending on the detection sequence configuration. The second conductor 312 can function as either a current source or a voltage measurement point during the detection sequence that moves sequentially around the plurality of conductors 112. When paired with the first conductor 310, the second conductor 312 forms a primary conductor path pair that enables measurement of a primary conductor path resistance through the biological tissue. The electrical field 332 generated between the first conductor 310 and second conductor 312 penetrates into and through the digit 14, allowing for impedance measurements that reflect blood flow characteristics within the capillaries 334 and blood vessel 330. Moreover, the second conductor 312 may participate in multiple conductor path pairs as the detection sequence progresses around the biometric ring 110.

In an illustrative configuration, the third conductor 314 may be positioned to create a secondary conductor path pair when combined with the first conductor 310, where one conductor separates the conductors within the plurality of conductors 112. The third conductor 314 enables measurement of a secondary conductor path resistance that provides different penetration depth characteristics compared to adjacent conductor pairs. The detection sequence can adopt a skip-one pattern where the current passes between the first conductor 310 and the third conductor 314, bypassing the second conductor 312 to achieve deeper tissue penetration. The electrical field patterns generated by the third conductor 314 may extend further into the digit 14 cross-section, potentially reaching deeper blood vessels and providing enhanced sensitivity to blood flow variations. Consequently, the third conductor 314 contributes to the generation of resistance maps that capture spatial variations in tissue conductivity.

The fourth conductor 316 may be configured to form a tertiary conductor path pair with the first conductor 310, where two conductors separate the conductors within the plurality of conductors 112. The fourth conductor 316 allows for skip-two detection patterns that achieve even greater penetration depths through the biological tissue. When current flows between the first conductor 310 and fourth conductor 316, the electrical field 332 may traverse a larger cross-sectional area of the digit 14, encompassing multiples of the capillaries 334 and potentially reaching central blood vessels. The fourth conductor 316 may also participate in quaternary conductor path pairs with other conductors in the array, contributing to comprehensive resistance mapping across the digit 14. Furthermore, the detection sequence may be customizable to determine optimal pairing configurations based on individual user characteristics and tissue properties.

The fifth conductor 318 may extend the conductor path pair options to include quinary configurations, where the detection sequence can select from various skip patterns to optimize signal quality. The fifth conductor 318 can be paired with conductors positioned at different angular separations around the biometric ring 110, allowing for adaptive detection sequences that learn optimal configurations for each user. The processor configured to perform the detection sequence may evaluate different pairing combinations involving the fifth conductor 318 to determine which arrangements provide the most reliable biometric readings. The electrical responses measured through the fifth conductor 318 contribute to the plurality of resistance maps that capture temporal variations in blood flow patterns. Additionally, the fifth conductor 318 may operate in detection sequences that move either clockwise or counterclockwise around the biometric ring 110.

In an illustrative configuration, the sixth conductor 320 may be positioned to enable senary conductor path pairs that provide additional flexibility in detection sequence design. The sixth conductor 320 can participate in various skip patterns, including skip-three, skip-four, or skip-five configurations, depending on the specific pairing arrangement selected by the processor. The detection sequence performed at a rate of 20-100 rotations per second may incorporate the sixth conductor 320 in multiple measurement cycles to capture rapid changes in blood flow dynamics. The electrical field 332 patterns generated through the sixth conductor 320 may interact with different regions of the capillaries 334 and blood vessel 330, providing spatial diversity in impedance measurements. Moreover, the sixth conductor 320 contributes to the comprehensive mapping of electrical conductivity variations across the digit 14 cross-section.

The seventh conductor 322 may enable septenary conductor path pairs that further expand the range of available detection patterns for customized measurement sequences. The seventh conductor 322 can be configured to work in conjunction with the processor that applies voltage or current with frequencies optimized for individual user sensitivity profiles. The detection sequence may incorporate the seventh conductor 322 in counterclockwise rotation patterns that provide alternative measurement perspectives compared to clockwise sequences. The electrical responses captured through the seventh conductor 322 contribute to the plurality of conductor path resistances that form the basis for biometric reading derivation. Thereafter, the seventh conductor 322 may participate in adaptive detection sequences that adjust pairing configurations based on real-time signal quality assessment.

The eighth conductor 324 may complete the conductor array configuration, enabling comprehensive coverage of the digit 14 circumference for complete resistance mapping. The eighth conductor 324 can participate in various conductor path pairs, including primary, secondary, tertiary, quaternary, quinary, senary, and septenary configurations, depending on the selected detection sequence pattern. The processor may utilize the eighth conductor 324 in customizable detection sequences that adapt to individual user characteristics and optimize measurement accuracy. The electrical field 332 generated through the eighth conductor 324 may interact with the skin 18, capillaries 334, and blood vessel 330 to provide comprehensive impedance data for biometric analysis. Alternatively, the eighth conductor 324 may serve as a reference point for sequential measurements that progress around the entire conductor array.

In an illustrative configuration, the blood vessel 330 may represent the primary vascular structure within the digit 14 that influences electrical conductivity measurements captured by the conductor array. The blood vessel 330 contains flowing blood that exhibits different electrical properties compared to the surrounding tissue, creating conductivity variations that can be detected through impedance measurements. The electrical field 332 patterns generated between conductor pairs may penetrate the blood vessel 330, allowing for the detection of blood flow dynamics and pressure variations. The blood vessel 330 may experience periodic changes in blood volume and flow velocity that correspond to cardiac cycles, creating temporal variations in the resistance maps derived from conductor measurements. Additionally, the blood vessel 330 may interact with the capillaries 334 to form a comprehensive vascular network that influences the overall impedance characteristics of the digit 14.

The electrical field 332 may represent the current pathways generated between conductor pairs during the detection sequence, penetrating through the skin 18 and biological tissue to enable impedance measurements. The electrical field 332 patterns may vary in depth and intensity depending on the specific conductor pair configuration and the skip pattern employed in the detection sequence. When current flows between adjacent conductors, the electrical field 332 may exhibit relatively shallow penetration, while skip-one or skip-two patterns may penetrate deeper into the electrical field 332 and into the digit 14. The electrical field 332 may interact with the blood vessel 330 and capillaries 334 to produce voltage responses that reflect blood flow characteristics and tissue conductivity variations. Consequently, the electrical field 332 serves as the mechanism through which the biometric ring 110 captures the electrical impedance data necessary for resistance map generation and biometric reading derivation.

Figure 4:
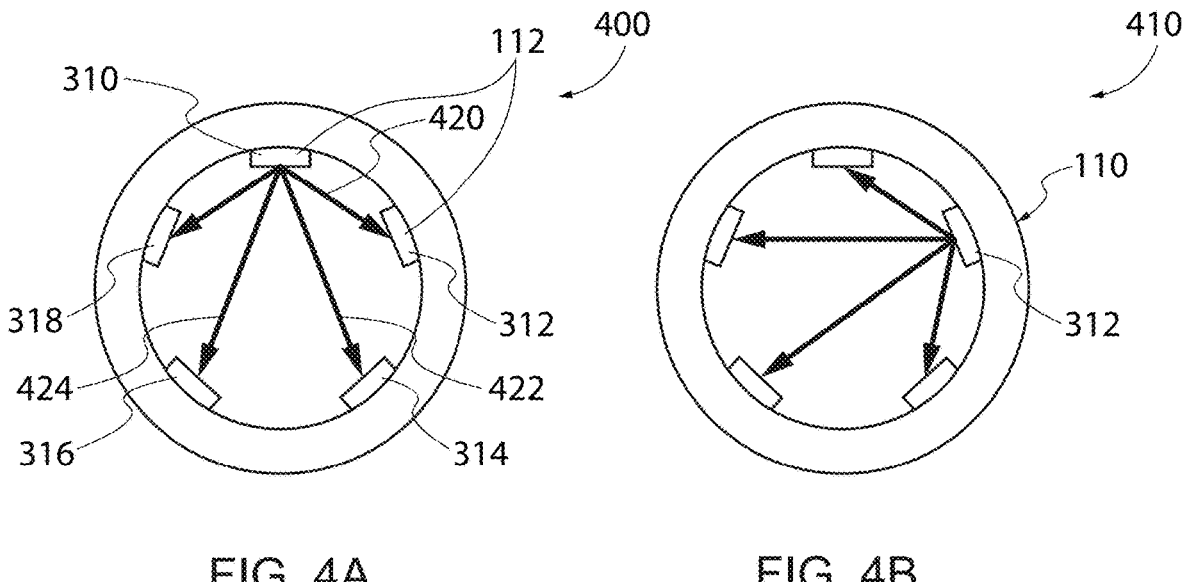
FIGS. 4A and 4B illustrate a biometric ring at two different measurement states showing conductor paths and electron flow, consistent with embodiments of the disclosure.

FIGS. 4A and 4B illustrate conductor path configurations according to various configurations. The biometric ring 110 may include a first reading illustration 400, a second reading illustration 410, a primary conductor path 420, a secondary conductor path 422, and a tertiary conductor path 424. The first reading illustration 400 and the second reading illustration 410 demonstrate different temporal states of the biometric ring 110 during operation, showing how the plurality of conductors 112 can be configured to create various measurement patterns across the digit 14.

The first reading illustration 400 shows the biometric ring 110 in a configuration where electrical current flows between specific conductor pairs within the plurality of conductors 112. The first conductor 310, second conductor 312, third conductor 314, fourth conductor 316, and fifth conductor 318 are arranged circumferentially around the inner surface of the biometric ring 110. In this configuration, the detection sequence moves sequentially around the plurality of conductors 112, establishing electrical connections between adjacent and non-adjacent conductor pairs. The arrows depicted in the first reading illustration 400 represent the flow of electrical current and the measurement of resistance across different conductor path pairs. This sequential measurement approach allows the biometric ring 110 to capture comprehensive electrical impedance data from multiple angles around the digit 14.

The second reading illustration 410 demonstrates an alternative conductor pairing configuration that occurs during the same detection sequence but at a different temporal moment. The second reading illustration 410 shows how the plurality of conductors 112 can be utilized to create different electrical field patterns through the biological tissue. The arrows in the second reading illustration 410 indicate different current flow paths compared to those shown in the first reading illustration 400, illustrating the dynamic nature of the measurement process. This temporal variation in conductor pairing enables the biometric ring 110 to generate multiple resistance measurements from different perspectives, contributing to the creation of comprehensive resistance maps.

In an illustrative configuration, the primary conductor path 420 represents the electrical connection between adjacent conductors within the plurality of conductors 112. The primary conductor path 420 may include a primary conductor path pair that comprises the first conductor 310 and the second conductor 312, or alternatively, the second conductor 312 and the third conductor 314. The primary conductor path 420 creates a relatively shallow penetration depth into the biological tissue of the digit 14, making this configuration particularly suitable for detecting blood flow patterns near the surface of the skin 18. The resistance measured across the primary conductor path 420 contributes to a primary conductor path resistance that forms part of the plurality of conductor path resistances used in generating the resistance maps.

The secondary conductor path 422 establishes electrical connections between conductors that are separated by one intermediate conductor within the plurality of conductors 112. The secondary conductor path 422 may include a secondary conductor path pair comprising the first conductor 310 and the third conductor 314, or the second conductor 312 and the fourth conductor 316. This configuration creates a deeper penetration of electrical fields into the biological tissue compared to the primary conductor path 420, allowing the biometric ring 110 to detect blood flow patterns at intermediate tissue depths. The secondary conductor path 422 generates a secondary conductor path resistance that provides complementary information to the primary conductor path resistance, enhancing the overall accuracy of the biometric measurements.

The tertiary conductor path 424 connects conductors that are separated by two intermediate conductors within the plurality of conductors 112, creating the deepest penetration pattern among the illustrated conductor path configurations. The tertiary conductor path 424 may include a tertiary conductor path pair comprising the first conductor 310 and the fourth conductor 316, or the second conductor 312 and the fifth conductor 318. This configuration enables the biometric ring 110 to detect blood flow patterns in deeper tissue layers, including one or more of the blood vessel 330 and capillaries 334 that may be located further from the skin 18 surface. The tertiary conductor path 424 produces a tertiary conductor path resistance that complements the primary conductor path resistance and secondary conductor path resistance, providing a comprehensive three-dimensional perspective of the electrical impedance characteristics within the digit 14.

Additionally, the biometric ring 110 may adopt additional sensing technologies such as photoplethysmography (PPG), electrocardiogram (ECG or EKG), bioimpedance (BioZ), galvanic skin response or electrodermal activity (GSR or EDA), and ultrasound to provide additional functionalities or refine blood pressure monitoring outputs. These supplementary sensing modalities can work in conjunction with the conductor path configurations shown in the first reading illustration 400 and second reading illustration 410 to enhance the accuracy and reliability of the biometric readings. The data from the biometric ring 110 can be converted into electrical images using statistical reconstruction methods based on Bayesian theory and maximum likelihood estimation, or deterministic reconstruction methods using back-projection algorithm, sensitivity matrix method, Calderon method, Newton's one-step error reconstructor method, Graz consensus Reconstruction algorithm for EIT (GREIT), and non-linear methods such as the D-bar method. These reconstruction techniques process the resistance data collected from the primary conductor path 420, secondary conductor path 422, and tertiary conductor path 424 to generate detailed cross-sectional images of blood flow patterns within the digit 14.

Figure 5:
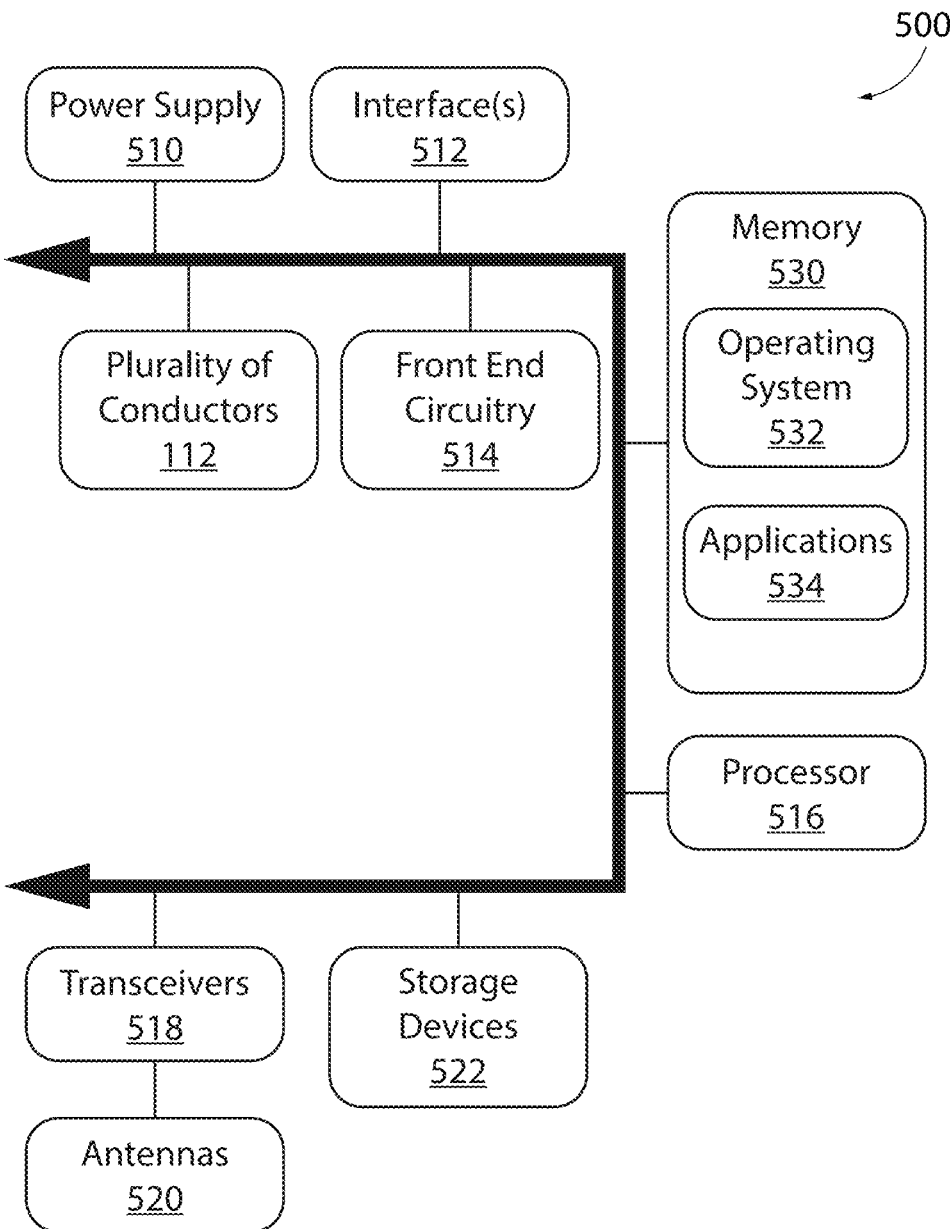
FIG. 5 illustrates a functional schematic of the biometric ring system showing key electronic components and their interconnections, consistent with embodiments of the disclosure.

FIG. 5 illustrates a functional schematic 500 detailing the electronic components and system architecture that enable the biometric ring 110 to perform measurements and data processing. The functional schematic 500 may include a power supply 510, interface(s) 512, front-end circuitry 514, a processor 516, transceiver(s) 518, antenna(s) 520, storage device(s) 522, memory 530, an operating system 532, and applications 534. These components work together in an integrated configuration to facilitate the collection, processing, and transmission of biometric data through the plurality of conductors 112.

The power supply 510 provides electrical energy to all components within the biometric ring 110 and may be configured as a rechargeable battery or other portable power source. The power supply 510 can be designed to support both continuous operation and spot check modes, where measurements are taken for specific durations, such as 10 seconds, before the system enters a low-power state to conserve battery life. Additionally, the power supply 510 may incorporate adaptive power management capabilities that adjust measurement frequency based on detected user activity levels or time of day patterns. During periods of low activity, the power supply 510 can reduce power allocation to non-critical components, while increasing power availability during exercise or when significant physiological changes are detected. The power supply 510 connects to all other components through internal power distribution pathways, ensuring stable voltage delivery across varying operational demands.

The interface(s) 512 serve as connection points between the electronic components and the plurality of conductors 112 positioned around the inner circumference of the biometric ring 110. The interface(s) 512 may include physical connectors, contact pads, or other electrical coupling mechanisms that establish reliable connections between the internal circuitry and the external conductors. These interfaces can be designed to accommodate different conductor materials, such as gold, silver, platinum, iridium, or other biocompatible and non-corroding materials. The interface(s) 512 may also incorporate switching mechanisms that allow the system to activate different conductor pairs during detection sequences selectively. Furthermore, the interface(s) 512 can support simultaneous reading from all electrical contacts when emitting from one sensor, rather than limiting operation to reading only one pair at a time, thereby enabling more comprehensive data collection.

In an illustrative configuration, the front-end circuitry 514 manages the electrical signal generation and measurement processes that occur between the plurality of conductors 112. The front-end circuitry 514 may include analog-to-digital converters, signal conditioning circuits, amplifiers, and filtering components that process the electrical responses measured through biological tissue. This circuitry can direct detection sequences using the plurality of conductors 112, controlling the timing and sequencing of current application and voltage measurement across different conductor path pairs. The front-end circuitry 514 may also incorporate frequency generation capabilities to apply electrical signals at specific frequencies, such as those ranging between 20 kHz and 100 kHz, depending on the measurement requirements and user characteristics. Additionally, the front-end circuitry 514 can include noise reduction and signal isolation features to ensure accurate measurement of the small electrical responses that occur through tissue.

The processor 516 serves as the central computational unit that coordinates all system operations and data processing functions within the biometric ring 110. The processor 516 may be configured to control the detection sequences that move sequentially around the plurality of conductors 112, managing the timing and coordination of measurements at rates ranging from 20 to 100 rotations per second. Moreover, the processor 516 can capture and/or process data utilized to generate a plurality of resistance maps by correlating voltage measurements and current flows across the plurality of conductor path pairs, transforming raw electrical data into meaningful spatial representations. The processor 516 may be utilized or otherwise enable later generation of cross-sectional images based on the plurality of resistance maps, utilizing computational algorithms to reconstruct two-dimensional or three-dimensional visualizations of blood flow patterns within the monitored tissue. Furthermore, the processor 516 (or other devices later utilized on-device or remote) can execute machine learning algorithms that correlate the plurality of resistance maps to blood biometric readings, processing successive frames of resistance map data collected over time to extract physiological parameters.

The transceiver(s) 518 and antenna(s) 520 work together to provide wireless communication capabilities for the biometric ring 110, enabling data transmission to external devices such as smartphones, tablets, or cloud-based systems. The transceiver(s) 518 may support multiple communication protocols, including Bluetooth, Wi-Fi, or other wireless standards, allowing flexible connectivity options depending on the target device and application requirements. The antenna(s) 520 can be integrated into the ring structure using flexible or compact designs that maintain the wearable form factor while providing adequate signal transmission and reception capabilities. These components enable the wireless communication transceiver to transmit biometric reading data to external devices, facilitating real-time monitoring and data analysis. The transceiver(s) 518 may also incorporate power management features that optimize transmission schedules to balance data delivery with battery conservation, particularly when the biometric ring 110 operates in adaptive power management modes.

The storage device(s) 522 provide non-volatile memory capabilities for storing measurement data, configuration settings, and system parameters within the biometric ring 110. These storage components can temporarily store biometric data when wireless transmission is not available or when power conservation strategies prioritize local storage over immediate transmission. The storage device(s) 522 may include flash memory, EEPROM, or other solid-state storage technologies that can withstand the physical stresses associated with wearable devices. Additionally, the storage device(s) 522 can maintain calibration data, user profiles, and historical measurement records that support personalized operation and long-term trend analysis. The storage capacity can be configured to accommodate multiple days or weeks of measurement data, depending on the sampling frequency and data compression techniques employed by the system.

In an illustrative configuration, the memory 530 provides volatile storage for active system operations and may include RAM or other high-speed memory technologies that support real-time data processing. The memory 530 houses the operating system 532, which manages the fundamental operations of the biometric ring 110, including task scheduling, resource allocation, and hardware abstraction. The operating system 532 can be implemented as a lightweight firmware-based system optimized for the power and processing constraints of wearable devices. Within the memory 530, applications 534 execute various specialized functions such as signal processing, data analysis, and user interface management. The applications 534 may include machine learning algorithms configured to correlate the plurality of resistance maps to blood biometric readings, processing temporal variations in measurement data to extract physiological parameters such as blood pressure, blood velocity, heart rate, and heart rate variability. These applications can also manage data formatting, compression, and transmission protocols that optimize the delivery of biometric information to external systems.

Figure 6:
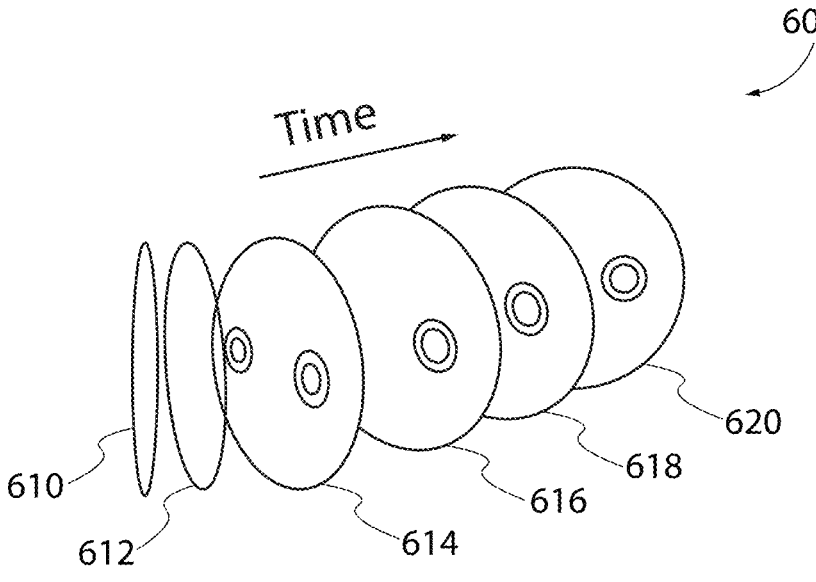
FIG. 6 illustrates a frame sequence schematic showing temporal data collection frames from the biometric ring, consistent with embodiments of the disclosure.

FIG. 6 illustrates a frame sequence schematic 600 according to various configurations. The frame sequence schematic 600 may include a first frame 610, a second frame 612, a third frame 614, a fourth frame 616, a fifth frame 618, and a sixth frame 620, all of which are resistance maps representing resistance of a cross-section (e.g., of the finger). These frames represent successive temporal data collection points that capture resistance measurements over time to enable dynamic biometric analysis. The sequential arrangement of frames demonstrates how the biometric ring 110 continuously gathers electrical impedance data from the plurality of conductors 112 positioned around the circumference of a digit 14.

The first frame 610 represents an initial temporal snapshot of electrical resistance measurements captured across the plurality of conductor path pairs. During this measurement period, the biometric ring 110 applies electrical current through the primary conductor path pair, secondary conductor path pair, and tertiary conductor path pair to generate corresponding resistance values. The first frame 610 establishes a baseline measurement that serves as a reference point for subsequent temporal analysis. The electrical impedance data collected during the first frame 610 contributes to the formation of resistance maps that characterize the cross-sectional electrical properties of the digit 14 at a specific moment in time.

The second frame 612 captures electrical resistance measurements at a subsequent time interval, typically milliseconds after the first frame 610. The temporal progression from the first frame 610 to the second frame 612 allows the system to detect changes in blood flow and tissue conductivity that occur during cardiac cycles. The second frame 612 may reveal variations in resistance values compared to the first frame 610, indicating dynamic physiological processes such as arterial pulsation or venous return. These temporal variations between frames provide the foundation for extracting biometric readings related to cardiovascular function.

The third frame 614 continues the sequential data collection process, capturing resistance measurements at a third temporal point in the measurement cycle. The progression through the first frame 610, second frame 612, and third frame 614 establishes a temporal pattern that enables the identification of periodic physiological signals. The third frame 614 may demonstrate further evolution of the resistance patterns as blood flow dynamics continue to change throughout the cardiac cycle. The accumulation of data across multiple frames allows for more robust signal processing and improved accuracy in biometric parameter extraction.

In an illustrative configuration, the fourth frame 616 represents a continuation of the temporal measurement sequence, providing additional data points for comprehensive physiological monitoring. The fourth frame 616 may capture resistance measurements during a different phase of the cardiac cycle compared to previous frames, potentially revealing peak systolic or diastolic conditions. The temporal spacing between frames can be adjusted to optimize the capture of relevant physiological signals while maintaining adequate sampling rates for accurate biometric analysis. The fourth frame 616 contributes to the overall dataset used for generating resistance maps and extracting biometric readings.

The fifth frame 618 extends the temporal measurement sequence further, capturing resistance data at an additional time point in the monitoring cycle. The progression through multiple frames, including the fifth frame 618, enables the detection of complex physiological patterns that may not be apparent from single-point measurements. The fifth frame 618 may reveal transitional states in blood flow or tissue conductivity that occur between major cardiac events. The continuous collection of frame data allows for the identification of subtle physiological variations that contribute to a comprehensive biometric assessment.

The sixth frame 620 completes the illustrated temporal sequence, demonstrating how the frame sequence schematic 600 captures multiple data points over time. The sixth frame 620 may represent a return to baseline conditions or the beginning of a new cardiac cycle, depending on the timing of the measurement sequence. The collection of data across all frames from the first frame 610 through the sixth frame 620 provides a comprehensive dataset for generating a plurality of resistance maps derived from the plurality of conductor path resistances. These resistance maps serve as the foundation for deriving biometric readings through advanced signal processing techniques.

The temporal progression through the frame sequence schematic 600 enables the processing of successive frames of resistance map data collected over time. A machine learning algorithm may be configured to analyze the temporal variations captured across the first frame 610, second frame 612, third frame 614, fourth frame 616, fifth frame 618, and sixth frame 620. The machine learning algorithm can incorporate deep neural network architectures with convolutional layers to capture spatial structure within individual frames, while recurrent components such as LSTM, transformer, RNN, or combinations thereof process temporal changes over the cardiac cycle. Additionally, fully connected layers for regression output enable the extraction of specific biometric parameters from the temporal frame sequence data. The integration of spatial and temporal analysis capabilities allows for the derivation of biometric readings from the plurality of resistance maps generated through the frame sequence schematic 600.

Figure 7:
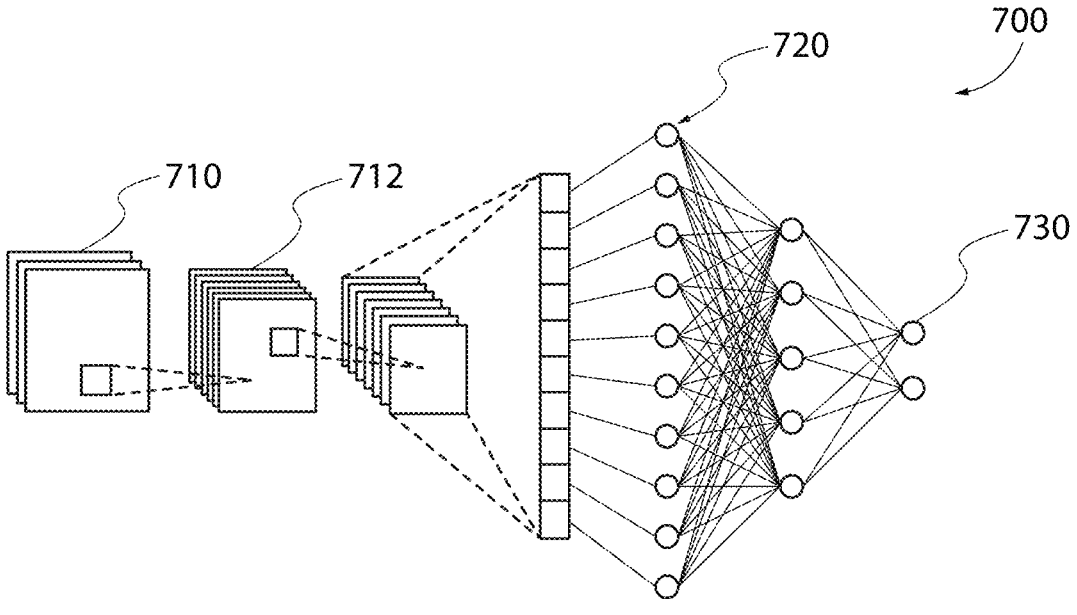
FIG. 7 illustrates a machine learning schematic showing the neural network architecture for processing biometric data, consistent with embodiments of the disclosure.

FIG. 7 illustrates a machine learning schematic 700 according to various configurations. The machine learning schematic 700 may include input(s) 710, preprocessing 712, a hidden layer 720, and output(s) 730. The machine learning schematic 700 demonstrates how neural network architecture processes resistance map data to generate biometric readings from the plurality of resistance maps collected by the biometric ring 110.

The input(s) 710 may receive successive frames of resistance map data collected over time from the plurality of conductors 112. The input(s) 710 can accept raw voltage measurements, processed impedance values, or cross-sectional images derived from the electrical resistance measurements. In some cases, the input(s) 710 may simultaneously receive multiple data streams representing different conductor path pairs, including primary conductor path pairs, secondary conductor path pairs, and tertiary conductor path pairs. The input(s) 710 can be configured to handle temporal sequences of resistance data, allowing the machine learning algorithm to analyze changes in blood flow patterns over cardiac cycles.

The preprocessing 712 may transform the raw resistance data into formats suitable for neural network analysis. The preprocessing 712 can perform signal normalization, artifact removal, temporal smoothing, and baseline correction on the incoming resistance measurements. Additionally, the preprocessing 712 may convert resistance values into cross-sectional images using statistical reconstruction methods based on Bayesian theory and maximum likelihood estimation. Alternatively, the preprocessing 712 can employ deterministic reconstruction methods using back-projection algorithms, sensitivity matrix methods, Calderon methods, Newton's one-step error reconstructor methods, Graz consensus Reconstruction algorithm for EIT (GREIT), or nonlinear methods such as D-bar methods. The preprocessing 712 may also generate two-dimensional impedance maps from electrical impedance values measured through the tissue of the body appendage.

In an illustrative configuration, the hidden layer 720 may comprise a deep neural network architecture with multiple processing components. The hidden layer 720 can include convolutional layers to capture spatial structure within the cross-sectional images of blood flow patterns. Moreover, the hidden layer 720 may incorporate recurrent components such as LSTM networks, transformer architectures, RNN structures, or combinations thereof to process temporal changes over cardiac cycles. The hidden layer 720 can analyze variations in the cross-sectional images over time to identify blood flow patterns and extract physiological parameters. Furthermore, the hidden layer 720 may include fully connected layers for regression output, enabling the correlation of resistance map variations to specific biometric readings.

The output(s) 730 may generate biometric readings derived from the processed resistance map data. The output(s) 730 can produce blood pressure measurements, blood velocity calculations, heart rate determinations, and heart rate variability assessments based on temporal changes in the plurality of resistance maps. The output(s) 730 may correlate blood flow patterns to blood biometric readings using the trained machine learning model implemented within the machine learning schematic 700. In some cases, the output(s) 730 can provide continuous monitoring data for cardiovascular assessment, enabling real-time analysis of physiological parameters extracted from the electrical impedance tomography data.

Figure 8:
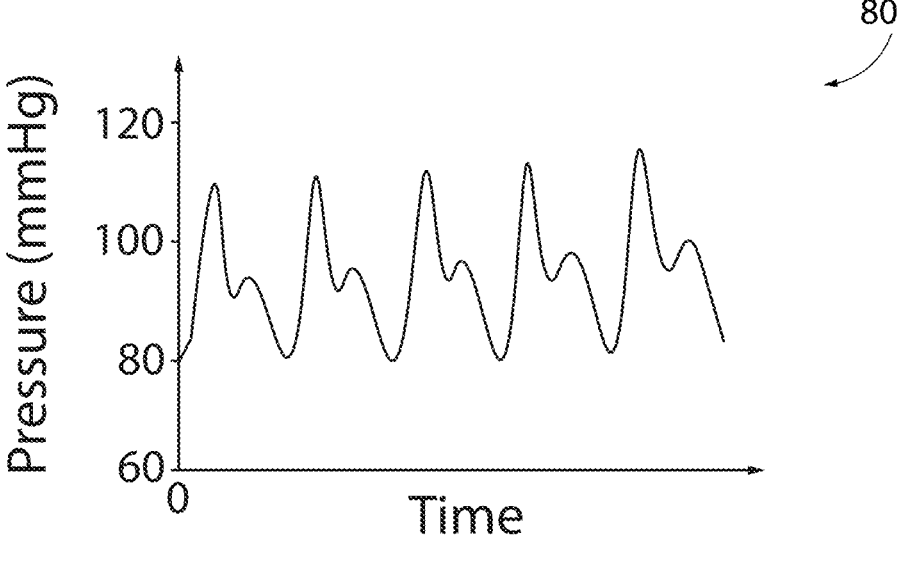
FIG. 8 illustrates a blood pressure measurement over time graph showing oscillating waveform patterns, consistent with embodiments of the disclosure.

FIG. 8 illustrates a blood pressure over time 800 output generated by the biometric ring system according to various configurations. The blood pressure over time 800 demonstrates how the system produces continuous blood pressure measurements through temporal analysis of resistance data collected from a plurality of conductors 112. The waveform characteristics displayed in the blood pressure over time 800 reflect physiological parameters that correlate directly to cardiovascular function and hemodynamic changes within the living being.

The blood pressure over time 800 may include oscillating waveform patterns that represent systolic and diastolic pressure variations throughout cardiac cycles. The waveform demonstrates regular peaks corresponding to systolic pressure measurements and valleys representing diastolic pressure readings, creating a rhythmic pattern that reflects the natural cardiac rhythm of the monitored individual. The amplitude variations within the blood pressure over time 800 provide information about pulse pressure, which may be calculated as the difference between systolic and diastolic values. Additionally, the temporal spacing between successive peaks enables determination of heart rate based on temporal changes in the plurality of resistance maps, as the processor 516 analyzes the cyclical nature of the pressure variations to extract cardiac timing information.

The blood pressure over time 800 facilitates continuous monitoring applications across multiple healthcare settings and use cases. In hospital and outpatient environments, the blood pressure over time 800 enables tracking of patient recovery progress, monitoring of medication effectiveness, and detection of early warning signs of cardiovascular complications through real-time pressure trend analysis. The continuous nature of the blood pressure over time 800 allows healthcare providers to observe gradual changes in cardiovascular status that might be missed during intermittent manual measurements. Moreover, the blood pressure over time 800 supports pharmaceutical clinical trials for drugs targeting cardiovascular conditions by providing comprehensive assessment data regarding the effects of experimental medications on participants' cardiovascular systems over extended monitoring periods.

In an illustrative configuration, the blood pressure over time 800 may be utilized for athletic performance optimization applications where athletes and coaches monitor cardiovascular response patterns during different types of exercise activities. The blood pressure over time 800 reveals recovery rates and overall fitness levels through analysis of pressure variations during physical exertion and subsequent recovery phases. Consequently, the blood pressure over time 800 enables occupational health and safety monitoring in industries with high-stress or physically demanding work environments, allowing continuous tracking of employee cardiovascular health during strenuous activities. The system generates alerts when the blood pressure over time 800 indicating potentially dangerous pressure elevations or irregular patterns that may compromise safety.

The blood pressure over time 800 supports sleep medicine applications by providing continuous blood pressure and blood flow data throughout nighttime monitoring periods. The waveform patterns within the blood pressure over time 800 during sleep cycles help diagnose and monitor sleep disorders that affect cardiovascular function, particularly conditions such as sleep apnea, where periodic pressure variations correlate with breathing interruptions. The blood pressure over time 800 reveals nocturnal hypertension patterns and blood pressure dipping characteristics that occur during normal sleep architecture. Furthermore, the blood pressure over time 800 enables detection of cardiovascular events that may occur during sleep, providing comprehensive monitoring data that supports clinical decision-making for sleep-related cardiovascular disorders.

Figure 9:
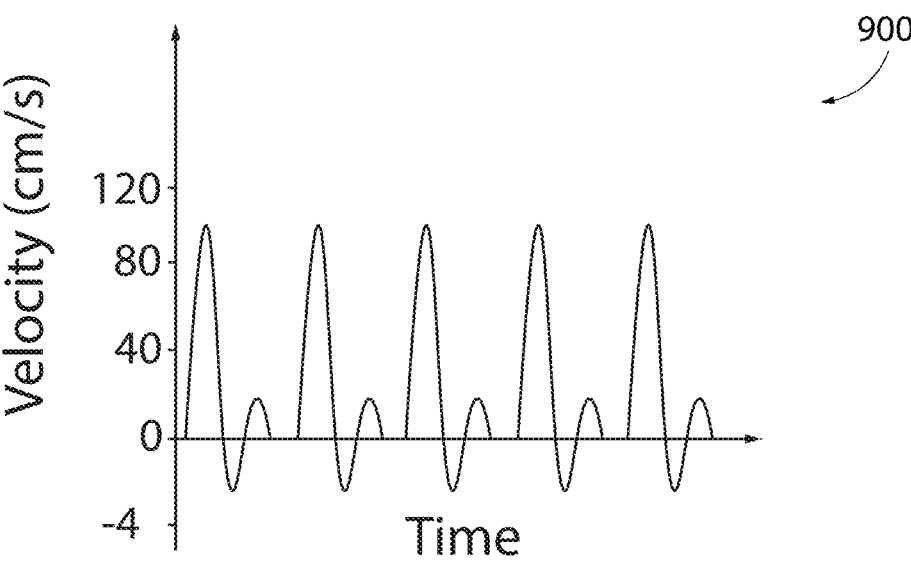
FIG. 9 illustrates a blood velocity measurement over time graph showing periodic velocity measurements, consistent with embodiments of the disclosure.

FIG. 9 illustrates a blood velocity over time 900 measurement output that demonstrates the dynamic tracking capabilities of the biometric ring system. The blood velocity over time 900 displays oscillating velocity patterns measured in centimeters per second (cm/sec) across temporal intervals, showing how blood flow dynamics change throughout cardiac cycles. The measurement data reveals periodic fluctuations that correspond to systolic and diastolic phases of the cardiovascular system, with velocity values ranging from negative to positive measurements that indicate directional blood flow characteristics within the monitored tissue.

The blood velocity over time 900 measurements may complement blood pressure readings by providing additional hemodynamic information that enhances comprehensive cardiovascular monitoring capabilities. Blood velocity data can reveal flow characteristics that blood pressure measurements alone cannot capture, such as flow obstructions, vessel compliance variations, and microcirculatory changes that occur within the finger tissue. The temporal patterns shown in the blood velocity over time 900 demonstrate how the biometric ring system can track rapid changes in blood flow that occur during each heartbeat, providing healthcare practitioners and users with detailed insights into cardiovascular function and potential circulatory abnormalities.

In an illustrative configuration, the blood velocity over time 900 measurements may be generated through analysis of the resistance map variations that occur as blood moves through vessels within the monitored tissue. The machine learning algorithm processes temporal changes in electrical impedance patterns to calculate velocity parameters, utilizing the relationship between blood volume changes and corresponding resistance fluctuations detected by the plurality of conductors. The system can differentiate between arterial and venous flow patterns by analyzing the timing and magnitude of velocity changes, allowing for more precise cardiovascular assessment than traditional monitoring methods that rely solely on pressure measurements.

Additionally, the blood velocity over time 900 data may be integrated with blood pressure measurements to calculate derived parameters such as pulse wave velocity, vascular resistance, and cardiac output estimates. The combination of velocity and pressure data enables the biometric ring system to provide comprehensive hemodynamic profiling that can detect early signs of cardiovascular disease, monitor treatment effectiveness, and track changes in vascular health over extended periods. The temporal resolution of the blood velocity over time 900 measurements allows for the detection of subtle flow variations that may indicate developing pathological conditions before they become clinically apparent through conventional monitoring approaches.

Figure 10:
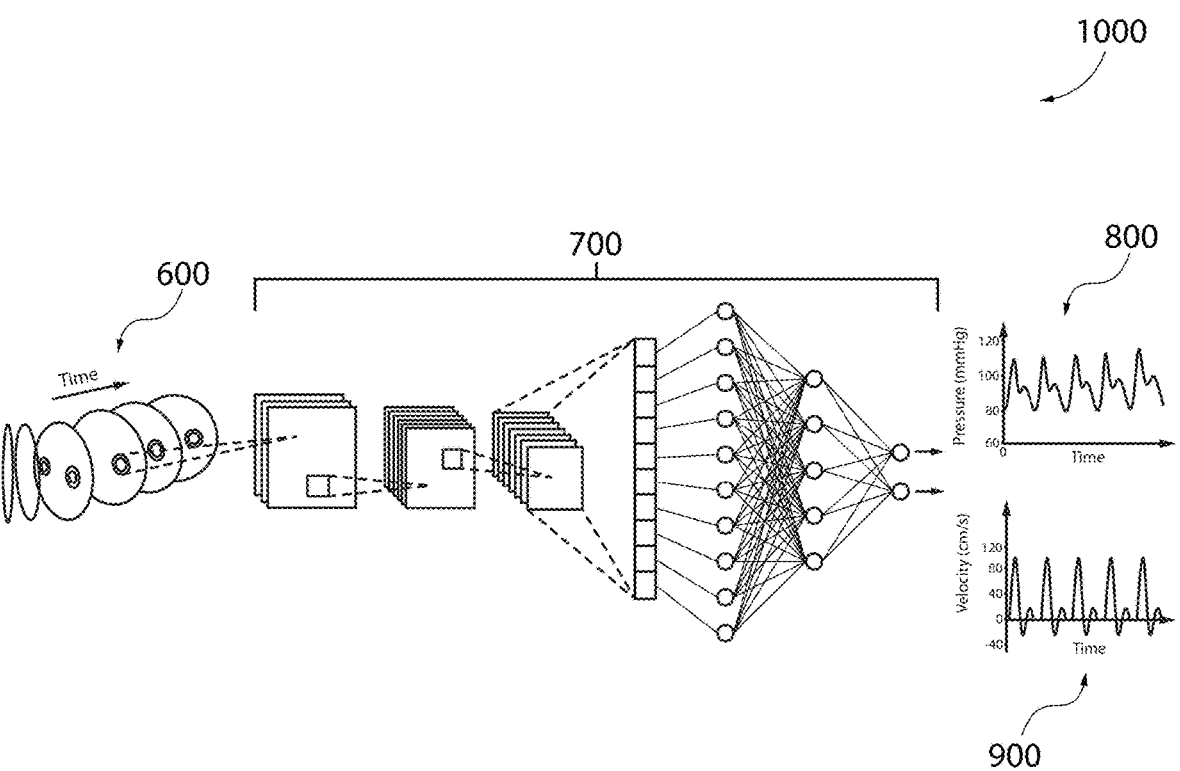
FIG. 10 illustrates a data processing flow from frame sequences through machine learning to blood pressure and velocity outputs, consistent with embodiments of the disclosure.

FIG. 10 illustrates a comprehensive system view 1000 that demonstrates the integration of data collection, processing, and output generation components within a biometric monitoring system. The integrated system may include a frame sequence schematic 600, a machine learning schematic 700, blood pressure over time 800, and blood velocity over time 900. These components work together to transform raw electrical measurements into meaningful physiological parameters through a coordinated process of data acquisition, algorithmic processing, and biometric output generation.

The frame sequence schematic 600 represents the initial data collection phase, where a ring-shaped device with a plurality of conductive elements distributed around its inner circumference captures sequential measurements. The frame sequence schematic 600 may include multiple temporal frames that document the electrical impedance variations as current flows through biological tissue. Each frame within the frame sequence schematic 600 corresponds to a complete rotation of measurements around the circumferential array of conductive elements. The sequential nature of these frames allows the system to capture dynamic changes in tissue conductivity that correlate with cardiovascular activity. Additionally, the frame sequence schematic 600 provides the foundational data structure that feeds into subsequent processing stages.

The machine learning schematic 700 serves as the central processing component that transforms raw impedance data into physiological insights. Circuitry configured to apply electrical signals between different combinations of the conductive elements and measure resulting electrical responses through biological tissue generates the input data for the machine learning schematic 700. The machine learning schematic 700 may include preprocessing stages that normalize and filter the incoming data streams from the frame sequence schematic 600. Moreover, the machine learning schematic 700 can create electrical impedance tomography data from the measured electrical responses, converting voltage and current measurements into spatial representations of tissue conductivity. The processing architecture within the machine learning schematic 700 can process the electrical impedance tomography data to generate cross-sectional images of blood flow within the biological tissue.

The blood pressure over time 800 represents one of the primary physiological outputs generated by the integrated system. A processing unit configured to extract physiological parameters from variations in the cross-sectional images over time produces the blood pressure over time 800 through analysis of temporal impedance patterns. The blood pressure over time 800 may display oscillating waveforms that correspond to systolic and diastolic pressure variations throughout cardiac cycles. Consequently, the blood pressure over time 800 provides continuous monitoring capabilities that can detect both acute changes and long-term trends in cardiovascular function. The waveform characteristics of the blood pressure over time 800 can indicate various physiological states and potential health conditions.

In an illustrative configuration, the blood velocity over time 900 complements the blood pressure measurements by providing additional cardiovascular parameters. The blood velocity over time 900 may be generated through analysis of the same impedance data processed by the machine learning schematic 700, but with different algorithmic approaches that focus on flow dynamics rather than pressure variations. The blood velocity over time 900 can reveal information about vascular health, blood flow patterns, and circulatory efficiency that may not be apparent from pressure measurements alone. Furthermore, the combination of blood pressure over time 800 and blood velocity over time 900 provides a comprehensive view of cardiovascular function that enhances diagnostic capabilities.

The integrated system operates through a coordinated sequence of data acquisition and processing steps that transform electrical measurements into physiological parameters. A method for non-invasive blood biometric reading may include positioning a plurality of electrical sensors in contact with skin around the circumference of a body appendage, as represented by the initial data collection phase. The system can apply current between sequential pairs of the electrical sensors while measuring voltage responses across the sequential pairs to determine electrical impedance values through the tissue of the body appendage. These measurements populate the frame sequence schematic 600 with temporal data that captures the dynamic nature of biological tissue conductivity.

The processing workflow continues with the construction of spatial representations from the temporal impedance measurements. The system can construct a two-dimensional impedance map of the body appendage from the electrical impedance values collected during the measurement sequence. This mapping process transforms the circumferential measurements into cross-sectional images that reveal the internal structure and conductivity distribution of the monitored tissue. The machine learning schematic 700 facilitates this transformation by applying sophisticated algorithms that can analyze temporal variations in the two-dimensional impedance map to identify blood flow patterns. These blood flow patterns serve as intermediate representations that bridge the gap between raw electrical measurements and physiological parameters.

The final stage of the integrated system involves correlating the identified blood flow patterns to blood biometric readings using a trained machine learning model. The machine learning schematic 700 may include neural network architectures that have been trained on datasets linking impedance patterns to known physiological states. The correlation process generates blood pressure over time 800 and blood velocity over time 900 outputs, providing clinically relevant information about cardiovascular function. Additionally, the integrated system can continuously update these outputs as new impedance data becomes available, enabling real-time monitoring of physiological changes. The seamless integration of all system components ensures that the biometric monitoring system can provide accurate, continuous, and non-invasive assessment of cardiovascular parameters.

Figure 11:
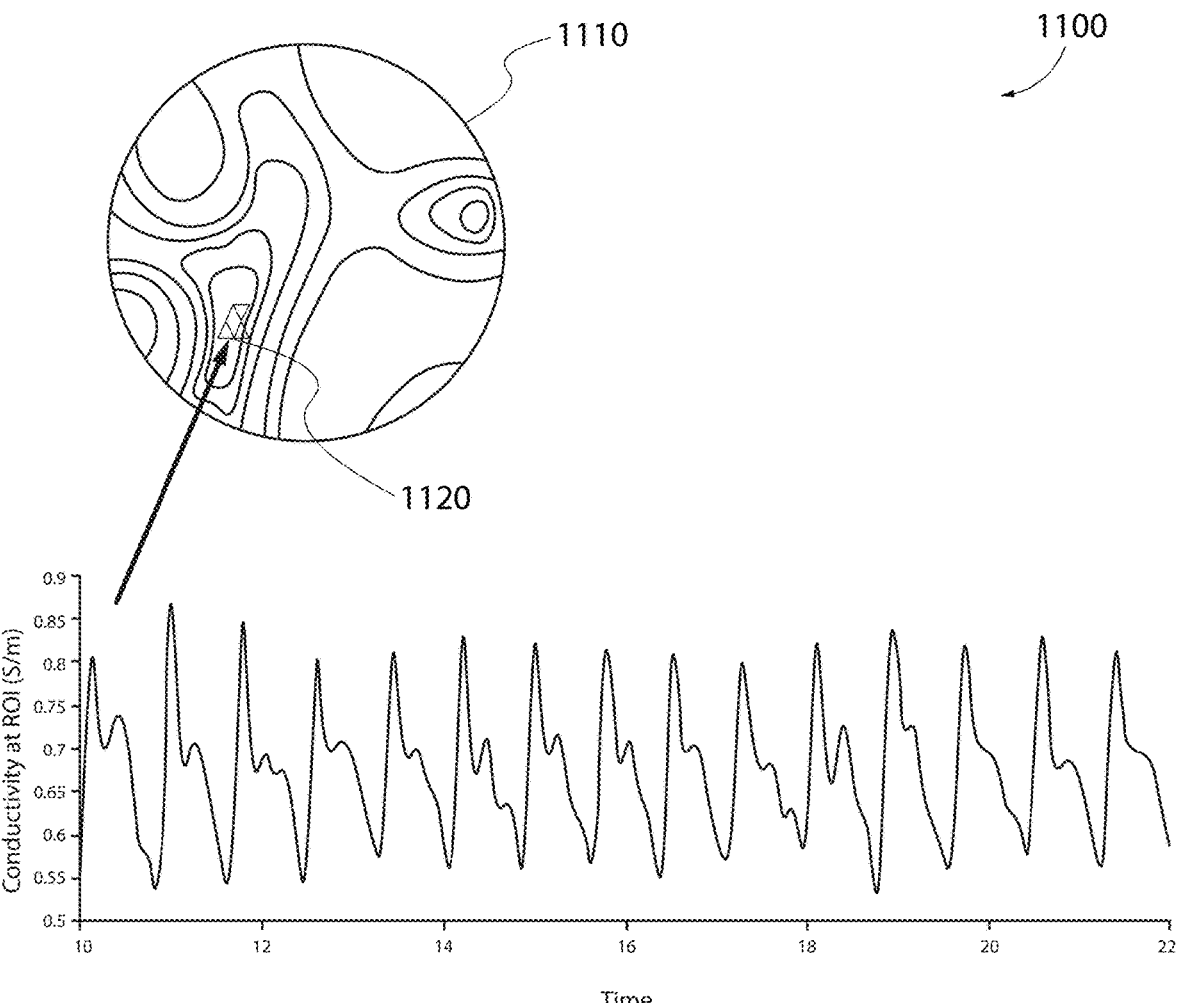
FIG. 11 illustrates a resistance over time measurement schematic with a magnified view of a specific measurement point, consistent with embodiments of the disclosure.

FIG. 11 illustrates a resistance over time schematic 1100 that demonstrates temporal analysis capabilities of the biometric monitoring system. The resistance over time schematic 1100 may include a resistance frame 1110 and a point of study 1120, which together enable a comprehensive analysis of physiological changes through electrical impedance variations. The resistance frame 1110 provides a visual representation of resistance measurements captured at specific temporal intervals, while the point of study 1120 identifies particular regions or time periods of interest within the resistance data. This temporal analysis framework allows the biometric ring to detect subtle changes in cardiovascular function that may indicate various physiological states or health conditions.

The resistance frame 1110 comprises a circular cross-sectional representation that displays resistance distribution patterns at a given moment in time. The resistance frame 1110 can be generated from the plurality of conductor path resistances measured across the circumferentially arranged conductors, creating a spatial map of electrical impedance within the monitored tissue. In some cases, the resistance frame 1110 may exhibit varying intensity levels or color gradations that correspond to different resistance values, with darker regions typically indicating higher resistance areas and lighter regions representing lower resistance zones. The resistance frame 1110 serves as a snapshot of the electrical properties of the tissue at a specific temporal point, enabling comparison with subsequent frames to identify changes over time.

The point of study 1120 represents a specific location or region within the resistance frame 1110 that has been identified for detailed analysis. The point of study 1120 may correspond to areas of particular physiological interest, such as regions with high blood vessel density or locations where significant resistance variations have been detected. In an illustrative configuration, the point of study 1120 can be automatically selected by the processing algorithms based on predetermined criteria, such as areas showing the greatest temporal variation or regions that correlate most strongly with known cardiovascular markers. Alternatively, the point of study 1120 may be manually designated by healthcare professionals or researchers for focused monitoring of specific anatomical features.

The temporal resistance analysis depicted in the resistance over time schematic 1100 enables detection of physiological changes through continuous monitoring of electrical impedance variations. As blood flows through vessels within the monitored tissue, the electrical conductivity of the tissue changes in response to blood volume variations, vessel dilation or constriction, and other hemodynamic factors. These changes manifest as temporal fluctuations in the resistance measurements captured by the biometric ring, creating characteristic patterns that can be analyzed to extract physiological information. The resistance over time schematic 1100 provides a framework for visualizing these temporal patterns and identifying clinically relevant changes in cardiovascular function.

Moreover, the resistance over time schematic 1100 facilitates the detection of cardiovascular events through pattern recognition and anomaly detection algorithms. The temporal resistance data can reveal characteristic signatures associated with various cardiovascular conditions, such as arrhythmias, blood pressure fluctuations, or vascular occlusions. By analyzing the resistance variations over extended time periods, the system can identify deviations from normal patterns that may indicate the onset of cardiovascular events or changes in overall cardiovascular health. The point of study 1120 allows for focused analysis of specific regions that may be particularly sensitive to certain types of cardiovascular changes, enhancing the system's ability to detect and characterize physiological events.

In an illustrative configuration, the resistance over time schematic 1100 can be integrated with machine learning algorithms to improve the accuracy and reliability of physiological parameter extraction. The temporal resistance patterns captured in successive frames of the resistance frames 1110 can serve as input data for trained neural networks that have learned to correlate specific resistance variation patterns with corresponding physiological states. The point of study 1120 can be dynamically adjusted based on the machine learning model's analysis, focusing attention on regions that provide the most informative data for specific physiological parameters or health conditions. This adaptive approach enhances the system's ability to provide accurate and clinically relevant biometric readings while minimizing the impact of noise or artifacts in the resistance measurements.

Figure 12:
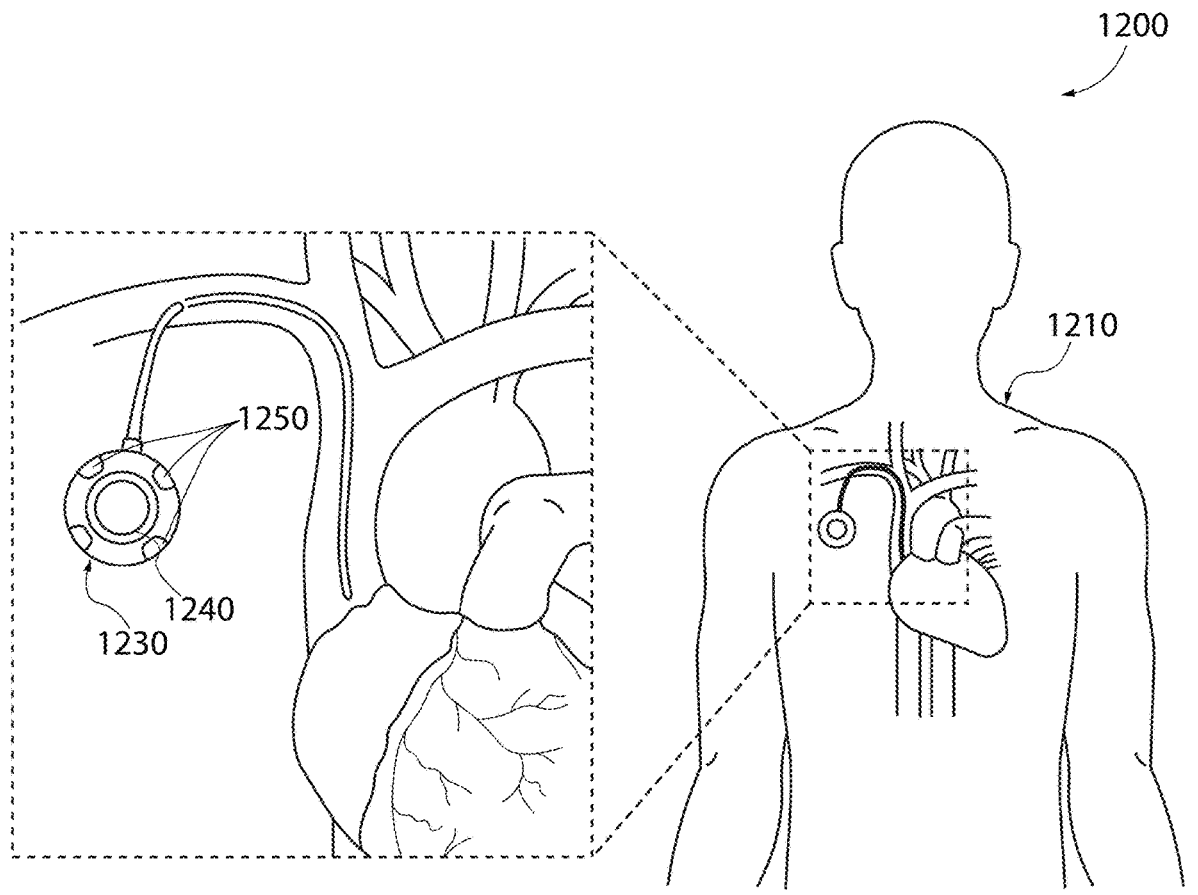
FIG. 12 illustrates a vascular-connected pathway embodiment showing the biometric ring integrated with a body port, consistent with embodiments of the disclosure.

FIG. 12 illustrates a vascular-connected pathway embodiment 1200 according to various configurations. The vascular-connected pathway embodiment 1200 may include a living being 1210, a port 1230, a biometric ring 1240, and a plurality of electrical contacts 1250. This configuration demonstrates how the biometric monitoring technology may be applied to different anatomical locations beyond traditional finger placement, expanding the versatility and applicability of the system across various body parts and medical scenarios.

The living being 1210 represents the biological subject being monitored and may include various anatomical structures where vascular access or monitoring may be beneficial. The living being 1210 may have multiple body parts that can be circumscribed and possess sufficient blood flow to render accurate blood pressure measurements. These body parts may include the wrist, neck, ankle, or any other anatomical location where vascular monitoring may be conducted. The living being 1210 provides the biological context for the monitoring system, with different anatomical locations offering varying degrees of vascular accessibility and measurement accuracy. Additionally, the living being 1210 may have different body contours and shapes that require adaptive device configurations to ensure proper contact and measurement reliability.

The port 1230 serves as a specialized vascular access point that may be surgically implanted or naturally occurring within the living being 1210. The port 1230 may be configured to provide direct access to the vascular system, allowing for enhanced monitoring capabilities compared to surface-based measurements. In medical applications, the port 1230 may represent a dialysis access point, chemotherapy port, or other medical device that requires continuous monitoring of blood flow and pressure. The port 1230 may have a cylindrical or tubular configuration that extends from the surface of the skin to connect with underlying vascular structures. Moreover, the port 1230 may be constructed from biocompatible materials that allow for long-term implantation without adverse biological reactions.

The biometric ring 1240 may be specifically configured to interface with the port 1230 and provide continuous monitoring of vascular parameters. The biometric ring 1240 may have a flexible and elastic construction that allows the device to conform closely with the contours of the port 1230 and surrounding tissue. This flexibility enables the biometric ring 1240 to maintain consistent contact with the monitoring site regardless of patient movement or positional changes. The biometric ring 1240 may be replaced with a band that has a closed band-shaped loop form factor, but may not necessarily be round to accommodate body parts that may not conform to a circular configuration. Consequently, the biometric ring 1240 may adapt to various anatomical shapes and sizes while maintaining the core functionality of electrical impedance monitoring.

In an illustrative configuration, the plurality of electrical contacts 1250 may be distributed around the circumference of the biometric ring 1240 to provide comprehensive electrical impedance measurements. The plurality of electrical contacts 1250 may be configured to emit current and measure voltage responses through the tissue surrounding the port 1230. These electrical contacts may be constructed from biocompatible and non-corroding materials such as gold, silver, platinum, or other precious metal alloys that ensure long-term stability in biological environments. The plurality of electrical contacts 1250 may be arranged in a concentric pattern that allows for multiple measurement pathways and enhanced spatial resolution of the impedance mapping. Furthermore, the plurality of electrical contacts 1250 may be individually addressable, allowing the system to select optimal contact pairs based on the specific anatomy and measurement requirements of each monitoring location.

The biometric ring 1240 may be worn on body parts other than fingers, demonstrating the versatility of the monitoring technology across different anatomical locations. The inner surface of the biometric ring 1240 may be configured to interface with a digit, an extremity, or a vascular-connected pathway of the living being 1210. This adaptability allows the monitoring system to be deployed in various clinical and non-clinical scenarios where vascular monitoring may be beneficial. The biometric ring 1240 may maintain its core electrical impedance measurement capabilities regardless of the specific body part being monitored, providing consistent and reliable biometric data across different anatomical locations. Additionally, the biometric ring 1240 may incorporate adaptive algorithms that account for the different electrical properties and vascular characteristics of various body parts to ensure accurate measurements.

Figure 13:
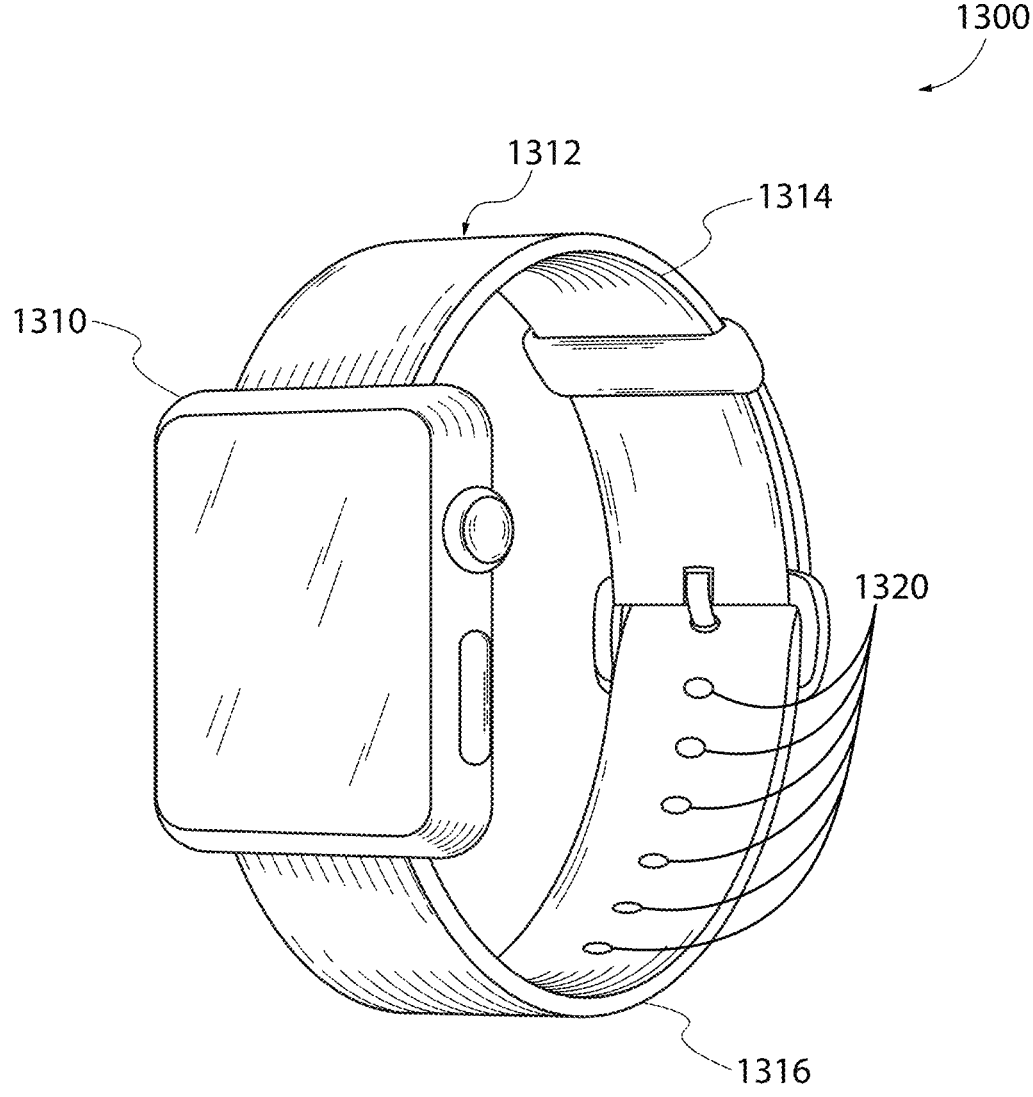
FIG. 13 illustrates a wearable electronics embodiment showing the biometric ring components integrated into a watch band assembly, consistent with embodiments of the disclosure.

FIG. 13 illustrates a wearable electronics embodiment 1300 according to various configurations. The wearable electronics embodiment 1300 may include a watch 1310, a band assembly 1312, a first band 1314, a second band 1316, and a plurality of contacts 1320. The wearable electronics embodiment 1300 demonstrates how the biometric monitoring technology can be adapted and integrated into conventional wearable form factors beyond traditional ring configurations. The watch 1310 serves as a central processing and display unit, while the band assembly 1312 provides the structural framework for housing the electrical measurement components. This configuration allows for expanded real estate and power management capabilities compared to more compact ring-based implementations.

The watch 1310 may include processing circuitry, display components, and power management systems that coordinate the biometric measurement operations. The watch 1310 can house the analog front-end circuitry, machine learning algorithms, and wireless communication transceivers that process and transmit the biometric data collected from the plurality of contacts 1320. Additionally, the watch 1310 may provide user interface capabilities, allowing individuals to view real-time biometric readings, configure measurement parameters, and access historical data trends. The watch 1310 can also manage power distribution to the band assembly 1312, ensuring consistent operation of the electrical measurement systems throughout extended monitoring periods.

The band assembly 1312 comprises the first band 1314 and the second band 1316, which together form a circumferential structure around a user's wrist or other body appendage. The band assembly 1312 may be constructed from flexible materials that conform to the contours of the user's anatomy while maintaining electrical contact integrity. The first band 1314 and second band 1316 can be configured to house different subsets of the plurality of contacts 1320, distributing the electrical measurement points around the circumference of the monitored body part. This distributed arrangement allows for comprehensive electrical impedance mapping across the cross-sectional area of the monitored tissue. Moreover, the band assembly 1312 may incorporate strain relief mechanisms and flexible interconnects that accommodate natural movement and positioning variations during wear.

In an illustrative configuration, the first band 1314 may contain a first subset of the plurality of contacts 1320, while the second band 1316 houses a complementary subset of electrical measurement elements. The first band 1314 can be positioned on one side of the wrist, providing electrical contact points that serve as current injection or voltage measurement locations during the detection sequence operations. The first band 1314 may incorporate biocompatible conductive materials such as gold, silver alloys, or platinum iridium to ensure reliable electrical contact with the skin surface. The first band 1314 can also include flexible printed circuit board elements that route electrical signals between the individual contact points and the processing circuitry housed within the watch 1310.

The second band 1316 operates in coordination with the first band 1314 to complete the electrical measurement circuits across the monitored tissue volume. The second band 1316 may contain additional contact elements from the plurality of contacts 1320 that serve as complementary measurement points for the electrical impedance tomography operations. The second band 1316 can be configured to maintain consistent electrical contact pressure against the skin surface, ensuring stable impedance measurements throughout the detection sequence cycles. Furthermore, the second band 1316 may incorporate adjustable tensioning mechanisms that allow users to optimize contact pressure for their individual anatomy and comfort preferences.

The plurality of contacts 1320 distributed across the first band 1314 and second band 1316 may operate using programmable detection sequences that adapt based on the user's physiological characteristics and measurement requirements. The plurality of contacts 1320 can employ swept frequency approaches using multiple frequencies ranging from 20 kHz to 100 kHz to gather data at different tissue depths for comprehensive information about blood flow and vessel characteristics. This multi-frequency capability allows the wearable electronics embodiment 1300 to penetrate various tissue layers and obtain detailed impedance profiles that correlate with cardiovascular parameters. Additionally, the plurality of contacts 1320 may dynamically select which pairs of contacts to use or adjust spacing between active contacts based on the detected tissue characteristics and measurement quality metrics. Consequently, the wearable electronics embodiment 1300 can optimize measurement accuracy and power consumption by adapting the detection sequence parameters to each user's anatomy and physiological state.

Figure 14:
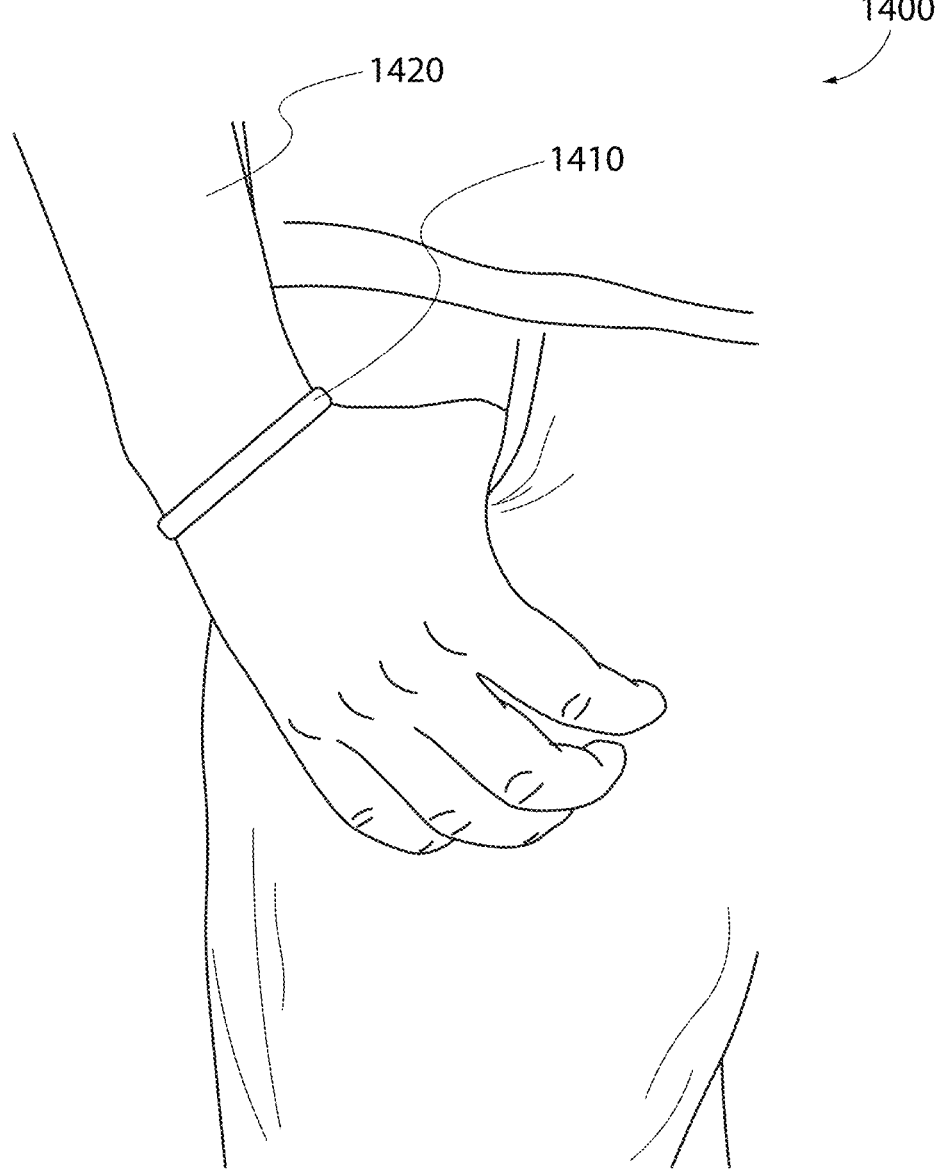
FIG. 14 illustrates a band configuration embodiment showing the biometric ring worn as a band on a human arm, consistent with embodiments of the disclosure.

FIG. 14 illustrates a band configuration 1400 showing a band 1410 positioned on an arm 1420 according to various configurations. The band configuration 1400 demonstrates the adaptability of the biometric monitoring technology to accommodate different anatomical locations and form factors beyond traditional ring applications. The band 1410 may include a flexible structure that can conform to the contours of the arm 1420, providing secure contact while maintaining comfort during extended wear periods. The arm 1420 represents one of several possible anatomical locations where the biometric monitoring system can be effectively deployed to measure physiological parameters through electrical impedance analysis.

The band 1410 may include a plurality of conductors circumferentially arranged about an inner surface configured to adjoin a living being. The conductors can be distributed around the inner circumference of the band 1410 to establish electrical contact with the skin of the arm 1420. In some cases, the band 1410 may provide at least four conductors to enable comprehensive electrical impedance measurements across the cross-sectional area of the arm 1420. The conductors may be configured to emit current and measure voltage in sequential patterns that move around the circumference of the band 1410. Additionally, the band 1410 can incorporate flexible printed circuit board technology that allows the conductive elements to maintain proper positioning and electrical connectivity even when the band 1410 flexes to accommodate different arm sizes and shapes.

The arm 1420 provides a larger cross-sectional area compared to finger applications, which may enable enhanced signal quality and improved measurement accuracy for certain physiological parameters. The increased tissue volume within the measurement field of the arm 1420 can provide stronger electrical signals and better signal-to-noise ratios during impedance measurements. Moreover, the arm 1420 location may offer access to larger blood vessels and more substantial blood flow patterns that can be detected through electrical impedance tomography techniques. The band 1410 positioned on the arm 1420 can apply voltage or current with a frequency between 20 kHz and 100 kHz to penetrate the tissue layers and generate measurable impedance variations corresponding to cardiovascular activity. Consequently, the band configuration 1400 extends the applicability of the biometric monitoring technology to users who may prefer wrist-worn devices or require larger form factors for enhanced measurement capabilities.

In an illustrative configuration, the band configuration 1400 may accommodate various anatomical dimensions and physiological characteristics across different user populations. The band 1410 can be manufactured in multiple sizes to fit different arm circumferences while maintaining optimal conductor spacing and contact pressure. The flexible nature of the band 1410 allows the device to adapt to the natural curvature and movement of the arm 1420 during daily activities. Furthermore, the band configuration 1400 may incorporate adjustable fastening mechanisms that enable users to achieve proper fit and contact pressure for reliable biometric measurements. The positioning of conductors within the band 1410 can be optimized for the specific anatomical characteristics of arm placement, taking into account the distribution of blood vessels, muscle tissue, and bone structures that influence electrical impedance patterns.

The methods, systems, devices, graphs, and/or tables are illustrative examples, and configurations may omit, substitute, or add various procedures or components as appropriate. For instance, the methods may be reordered in alternative configurations, and/or various stages may be added, omitted, and/or combined. Alternatively, features described with respect to certain configurations may be in various alternative configurations. Different aspects and elements of the configurations may be combined similarly. Also, technology evolves; thus, many of the elements are examples and do not limit the scope of the disclosure or claims. Additionally, the techniques discussed herein may provide differing results with different types of context awareness classifiers.

According to another aspect of the present disclosure, a biometric ring is provided. The biometric ring comprises an inner surface configured to adjoin a living being. The biometric ring includes a plurality of conductors circumferentially arranged about the inner surface and configured to emit voltage and measure voltage. The biometric ring comprises a plurality of conductor path pairs comprising at least a primary conductor path pair, a secondary conductor path pair, and a tertiary conductor path pair. The biometric ring includes a plurality of conductor path resistances comprising at least a primary conductor path resistance, a secondary conductor path resistance, and a tertiary conductor path resistance. The biometric ring comprises a plurality of resistance maps derived from the plurality of conductor path resistances. The biometric ring includes a biometric reading derived from a plurality of resistance maps.

According to other aspects of the present disclosure, the biometric ring may include one or more of the following features. The inner surface may be configured to interface with a digit, an extremity, or a vascular-connected pathway of the living being. The plurality of conductors may comprise a first conductor, a second conductor separated from the first conductor, and a resistance measured between the first conductor and the second conductor, the resistance operationally associated with a voltage potential and a current flow between the first conductor and the second conductor. The plurality of conductor path pairs may further comprise at least one of a quaternary conductor path pair, a quinary conductor path pair, a senary conductor path pair, and a septenary conductor path pair. The primary conductor path pair may comprise adjacent conductors within the plurality of conductors. The secondary conductor path pair may comprise conductors separated by one conductor within the plurality of conductors. The tertiary conductor path pair may comprise conductors separated by two conductors within the plurality of conductors. The biometric reading may comprise at least one of blood pressure, blood velocity, heart rate, and heart rate variability. The biometric ring may further comprise a processor configured to generate the plurality of resistance maps by correlating voltage measurements and current flows across the plurality of conductor path pairs.

According to another aspect of the present disclosure, a biometric monitoring system is provided. The biometric monitoring system comprises a ring-shaped device having an inner circumference with a plurality of conductive elements distributed around the inner circumference. The bio-metric monitoring system includes circuitry configured to apply electrical signals between different combinations of the conductive elements and measure resulting electrical responses through biological tissue. The biometric monitoring system comprises a processing unit configured to create electrical impedance tomography data from the measured electrical responses, process the electrical impedance tomography data to generate cross-sectional images of blood flow within the biological tissue, and extract physiological parameters from variations in the cross-sectional images over time.

According to another aspect of the present disclosure, a method for non-invasive blood biometric reading is provided. The method comprises positioning a plurality of electrical sensors in contact with the skin around the circumference of a body appendage. The method includes applying a current between sequential pairs of the electrical sensors. The method comprises measuring voltage responses across the sequential pairs to determine electrical impedance values through the tissue of the body appendage. The method includes constructing a two-dimensional impedance map of the body appendage from the electrical impedance values. The method comprises analyzing temporal variations in the two-dimensional impedance map to identify blood flow patterns. The method includes correlating the blood flow patterns to blood biometric readings using a trained machine learning model.

Unless defined otherwise, all technical and scientific terms used herein have the same meaning as commonly or conventionally understood. As used herein, the articles "a" and "an" refer to one or more than one (i.e., to at least one) of the grammatical object of the article. By way of example, "an element" means one element or more than one element. "About" and/or "approximately" as used herein when referring to a measurable value such as an amount, a temporal duration, and the like encompass variations of ±20% or ±10%, ±5%, or ±0.1% from the specified value as such variations are appropriate in the context of the systems, devices, circuits, methods, and other implementations described herein. "Substantially," as used herein when referring to a measurable value such as an amount, a temporal duration, a physical attribute (such as frequency), and the like, also encompasses variations of ±20% or ±10%, ±5%, or ±0.1% from the specified value as such variations are appropriate in the context of the systems, devices, circuits, methods, and other implementations described herein.

As used herein, including in the claims, "and" as used in a list of items prefaced by "at least one of" or "one or more of" indicates that any combination of the listed items may be utilized. For example, a list of "at least one of A, B, and C" includes any of the combinations A, B, C, AB, AC, BC, and/or ABC (i.e., A, B, and C). Furthermore, to the extent more than one occurrence or use of the items A, B, or C is possible, multiple uses of A, B, and/or C may form part of the contemplated combinations. For example, a list of "at least one of A, B, and C" may include AA, AAB, AAA, BB, etc.

While illustrative and presently preferred embodiments of the disclosed systems, methods, and/or machine-readable media have been described in detail herein, it is to be understood that the inventive concepts may be otherwise variously embodied and employed and that the appended claims are intended to be construed to include such variations except as limited by the prior art. While the principles of the disclosure have been provided in connection with specific apparatuses and methods, it is to be clearly understood that this description is made only by way of example and not as a limitation on the scope of the disclosure.

What is claimed is:

1. A biometric ring comprising:
   a ring-shaped housing having an inner circumferential surface configured to adjoin a living being;
   a plurality of conductors circumferentially arranged about the inner circumferential surface and, the plurality of conductors being configured to emit an electrical current and measure a voltage;
   a plurality of conductor paths comprising at least:
      a primary conductor path between a first conductor and an adjoining second conductor of the plurality of conductors;
      a secondary conductor path between the first conductor and a third conductor of the plurality of conductors; and
      a tertiary conductor path between the first conductor and a fourth conductor of the plurality of conductors;
   a plurality of conductor path resistances comprising at least:
      a primary conductor path resistance of the primary conductor path;
      a secondary conductor path resistance of the secondary conductor path; and
      a tertiary conductor path resistance of the tertiary conductor path;
   a current generation circuitry configured to apply the electrical current through selected paths of the plurality of conductor paths;
   a voltage measurement circuitry configured to measure the voltage across each path of the plurality of conductor paths; and
   a processor configured to:
      generate a plurality of resistance maps from the plurality of conductor path resistances using:
         an electrical impedance tomography reconstruction algorithm and a detection sequence that moves sequentially around the plurality of conductors at a rate of 20-100 rotations per second; and
      derive a blood biometric reading from the plurality of resistance maps according to temporal variation in the plurality of resistance maps, wherein the blood biometric reading comprises at least one of:
         a blood pressure, and
         a blood velocity.

2. The biometric ring of claim 1, wherein the inner circumferential surface is sized to interface with a digit, an extremity, or a vascular-connected pathway of the living being.

3. The biometric ring of claim 2, wherein the plurality of conductor paths are configured to pierce through the digit, extremity, or vascular connected pathway of the living being.

4. The biometric ring of claim 1, wherein the plurality of conductors comprises more than four conductors.

5. The biometric ring of claim 1 wherein the processor is configured to apply the current with a frequency between 20 kHz and 100 kHz.

6. The biometric ring of claim 1, further comprising a machine learning algorithm to correlate the plurality of resistance maps to the blood biometric reading.

7. The biometric ring of claim 6, wherein the machine learning algorithm is configured to process successive frames of resistance map data collected over time to improve the blood biometric reading.

8. The biometric ring of claim 1, further comprising analog front-end circuitry to direct a detection sequence using the plurality of conductors.

9. The biometric ring of claim 1, further comprising a wireless communication transceiver to transmit the blood biometric reading to an external device.

10. The biometric ring of claim 1, wherein the processor is configured to generate a plurality of cross-sectional images based on the plurality of resistance maps.

11. The biometric ring of claim 10, wherein the plurality of cross-sectional images are generated using at least one of a statistical reconstruction method and a deterministic reconstruction method.

12. The biometric ring of claim 1, wherein the processor is configured to determine heart rate based on temporal changes in the plurality of resistance maps.

13. A method for blood biometric monitoring comprising:
   positioning a ring-shaped housing comprising:
      an inner circumferential surface to adjoin a living being; and
      a plurality of conductors about the inner circumferential surface;
   emitting current from the plurality of conductors;
   establishing a plurality of conductor path pairs comprising at least:
      a primary conductor path pair;
      a secondary conductor path pair; and
      a tertiary conductor path pair;
   determining a plurality of conductor path resistances comprising at least:
      a primary conductor path resistance between the primary conductor path pair;
      a secondary conductor path resistance between the secondary conductor path pair; and
      a tertiary conductor path resistance between the tertiary conductor path pair;
   generating performing a detection sequence that moves sequentially around the plurality of conductors at a rate of 20-100 rotations per second; a plurality of resistance maps derived from the plurality of conductor path resistances; and
   deriving at least one of a blood pressure or a blood velocity of a blood biometric reading from the plurality of resistance maps.

14. The method of claim 13, wherein positioning the inner circumferential surface comprises:
   interfacing with a digit, an extremity, or a vascular-connected pathway of the living being.

15. The method of claim 13, wherein establishing the plurality of conductor path pairs comprises:
   providing a first conductor;
   providing a second conductor separated from the first conductor; and
   measuring a resistance between the first conductor and the second conductor, the resistance operationally associated with a voltage potential and the current flow between the first conductor and the second conductor.

16. The method of claim 13, further comprising applying the current with a frequency between 20 kHz and 100 kHz.

* * * * *